United States Patent
Talmer et al.

(10) Patent No.: US 12,018,248 B2
(45) Date of Patent: Jun. 25, 2024

(54) SAMPLE PROCESSING DEVICES, SYSTEMS AND METHODS

(71) Applicant: Abbott Molecular Inc., Des Plaines, IL (US)

(72) Inventors: Mark Talmer, Pepperell, MA (US); Jody L. Keck, Abbott Park, IL (US); Wesley W. Addison, Chicago, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 518 days.

(21) Appl. No.: 17/140,854

(22) Filed: Jan. 4, 2021

(65) Prior Publication Data

US 2021/0189380 A1    Jun. 24, 2021

Related U.S. Application Data

(63) Continuation of application No. 15/459,680, filed on Mar. 15, 2017, now Pat. No. 10,907,147.

(60) Provisional application No. 62/308,645, filed on Mar. 15, 2016.

(51) Int. Cl.
| | |
|---|---|
| *G01N 1/12* | (2006.01) |
| *B01L 99/00* | (2010.01) |
| *C12N 15/10* | (2006.01) |
| *G01N 33/543* | (2006.01) |
| *G01N 35/00* | (2006.01) |
| *G01N 35/10* | (2006.01) |

(52) U.S. Cl.
CPC .......... *C12N 15/1013* (2013.01); *B01L 99/00* (2013.01); *C12N 15/1003* (2013.01); *G01N 1/12* (2013.01); *G01N 33/543* (2013.01); *G01N 35/0098* (2013.01); *G01N 35/10* (2013.01); *G01N 35/1065* (2013.01); *B01L 2200/0668* (2013.01); *B01L 2400/043* (2013.01); *G01N 2035/1053* (2013.01)

(58) Field of Classification Search
CPC ....... B01L 2200/0668; B01L 2400/043; B01L 99/00; C12N 15/1003; C12N 15/1013; G01N 1/12; G01N 2035/1053; G01N 33/543; G01N 35/0098; G01N 35/10; G01N 35/1065
See application file for complete search history.

(56) References Cited

U.S. PATENT DOCUMENTS

| | | |
|---|---|---|
| 6,830,935 B1 | 12/2004 | El-Amin et al. |
| 7,442,186 B2 | 10/2008 | Blomquist |
| 2004/0024366 A1 | 2/2004 | Tsai |
| 2006/0171851 A1 | 8/2006 | Squirrell |

(Continued)

FOREIGN PATENT DOCUMENTS

| | | |
|---|---|---|
| CN | 205737245 | 12/2016 |
| WO | 2017160979 | 9/2017 |

(Continued)

*Primary Examiner* — Lydia Edwards
(74) *Attorney, Agent, or Firm* — Edward J. Baba; Mandar A. Joshi; Bozicevic, Field & Francis LLP

(57) ABSTRACT

This instant disclosure provides methods of processing a sample in an automated sample processing device including devices configured for the automated extraction or isolation of nucleic acids. Also provided are plungers for use in such devices and methods of sample processing. Systems for performing the described methods and employing the described plungers are also provided.

17 Claims, 12 Drawing Sheets

(56) References Cited

U.S. PATENT DOCUMENTS

| | | | |
|---|---|---|---|
| 2007/0087431 A1* | 4/2007 | Ching | B01L 7/00 |
| | | | 435/306.1 |
| 2011/0183433 A1 | 7/2011 | Motadel et al. | |
| 2013/0078625 A1* | 3/2013 | Holmes | G01N 35/0092 |
| | | | 204/601 |
| 2014/0276592 A1 | 9/2014 | Mottola et al. | |
| 2015/0125939 A1 | 5/2015 | Squirrell | |

FOREIGN PATENT DOCUMENTS

| | | |
|---|---|---|
| WO | 2017161046 | 9/2017 |
| WO | 2017161053 | 9/2017 |
| WO | 2017161056 | 9/2017 |
| WO | 2017161058 | 9/2017 |

* cited by examiner

Sample Preparation
(with or without pretreatment)

Sample Lysis

Sample Washing

Elution

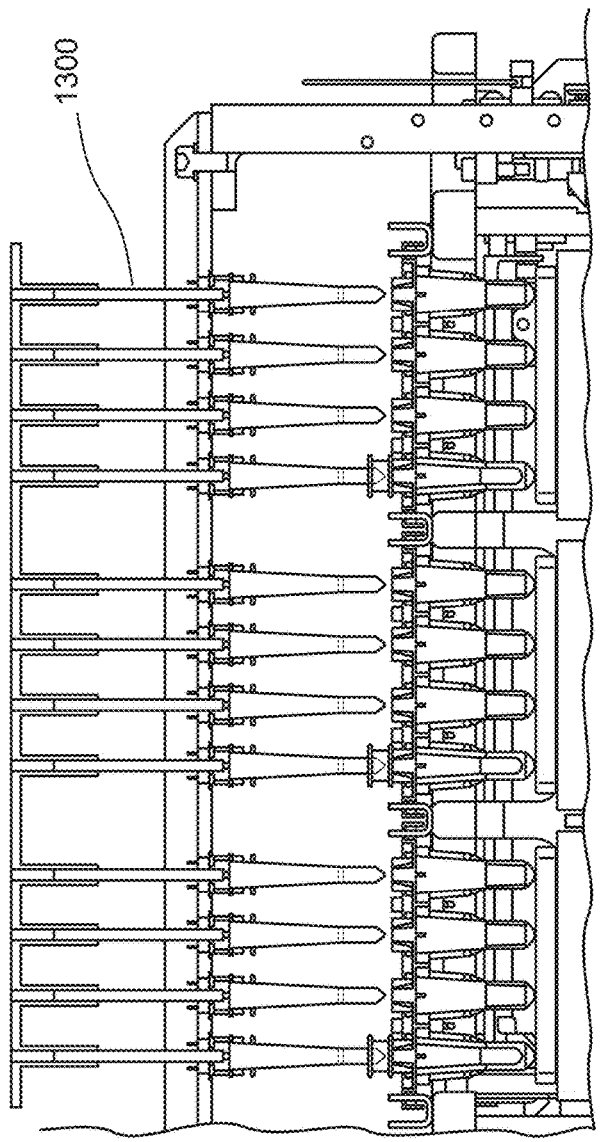
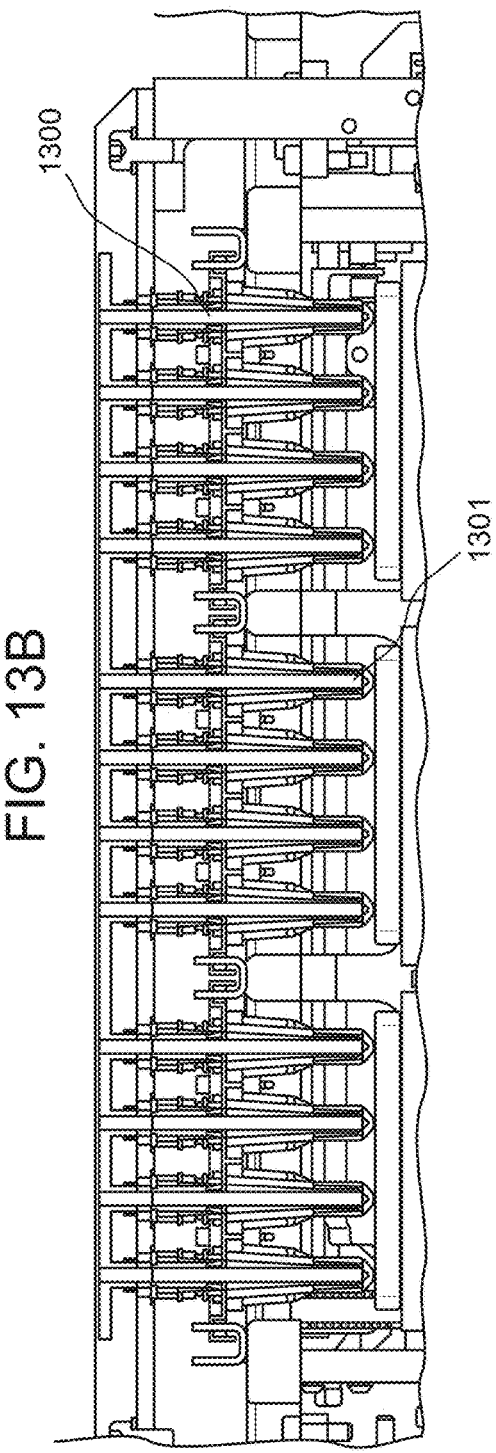
FIG. 13A
FIG. 13B

SAMPLE PROCESSING DEVICES, SYSTEMS AND METHODS

CROSS-REFERENCE TO RELATED APPLICATIONS

Pursuant to 35 U.S.C. § 119(e), this application claims priority to the filing date of the U.S. Provisional Patent Application Ser. No. 62/308,645, filed Mar. 15, 2016, the disclosure of which application is herein incorporated by reference.

BACKGROUND

Molecular diagnostics is a technique increasingly relied upon by clinicians to make informed clinical decisions. Many of the diagnostic assays are performed by an analytical technician. Dramatic advances in analytic instrumentation and information management systems have shifted the role of the technician from diagnostic assay measurements to sample extraction and processing. In large clinical testing facilities, where hundreds of assays are performed daily, many of the tasks performed by an analytical technician have been replaced by automated systems. Automated systems used in clinical testing facilities allow for high speed, throughput and consistency in the execution of diagnostic assays.

As the demand from clinicians and patients for diagnostic tests has increased, the stringency of requirements for higher assay sensitivity, selectivity, precision and throughput has increased correspondingly. The reliability of diagnostic assays depends on the consistency and quality of sample input. In highly sensitive assays, such as those based on real-time PCR techniques, the quality of the input sample directly correlates with the quality in the results.

SUMMARY

Aspects of the instant disclosure include plungers for sample processing, systems for sample processing using a plunger and a sample processing well, and methods for eluting nucleic acids.

Aspects of the instant disclosure include a plunger for sample processing in an automated sample processing device where the plunger includes an elongated hollow cone structure that includes an open top, a closed rounded tip with an end nub and a plurality of flutes arranged parallel to the long axis of the elongated hollow cone structure that extend from the closed rounded tip less than the entire length of the elongated hollow cone structure.

In some aspects, the plunger includes a plurality of flutes that extend from the closed rounded tip less than half the entire length of the elongated hollow cone structure. In some aspects, the plunger includes an elongated hollow cone structure that is configured to receive a plunger magnet inserted through the open top. In some aspects, the plunger is configured to receive a plunger magnet that has a maximum diameter essentially equal to the minimum diameter inside the hollow cone structure of the plunger. In some aspects, the plunger includes an elongated hollow cone structure that includes a wall with a nominal thickness between 0.15 mm to 0.45 mm. In some aspects, the plunger includes an elongated hollow cone structure that includes a maximum diameter adjacent to the closed rounded tip that is equal to the smallest diameter of a sample processing well. In some aspects, the plunger includes a volume of space ascribed to the flutes that is determined from the difference in volume between the plunger and an identical plunger without the plurality of flutes that is between 10 $mm^3$ and 100 $mm^3$. In some aspects, the plunger includes a plurality of flutes that is three or more flutes, four or more flutes, five or more flutes or six flutes or more. In some aspects, the plunger includes an elongated hollow cone structure that includes two or more different tapers including where the two or more different tapers include a first taper adjacent to the fluted region and a second taper adjacent to the open top. In some aspects, the plunger includes two or more tapers where the first taper is greater than the second taper. In some aspects, the plunger includes a plunger holder element that is configured to allow coupling of the plunger to a plunger manipulator. In some aspects, the plunger holder element is essentially a flange encircling the open top. In some aspects, the plunger includes an elongated hollow cone structure that includes a stacking spacer including where the stacking spacer includes a flange encircling the circumference of the hollow cone structure or where the stacking spacer includes a plurality of aligned ribs arranged parallel with the long axis of the elongated hollow tube.

Aspects of the instant disclosure include a system for sample processing in an automated sample processing device that includes a sample processing well, a plunger that includes an elongated hollow cone structure that includes: an open top; a closed rounded tip comprising an end nub; a diameter adjacent to the closed rounded tip equal to the smallest diameter of the sample processing well; and a plurality of flutes arranged parallel to the long axis of the elongated hollow cone structure extending from the closed rounded tip. Aspects of such systems include where the sample processing well is configured to receive and align the plunger to the center of the sample processing well when the plunger is inserted into the sample processing well.

In some aspects, the system includes where the sample processing well includes a cone shaped bottom or a dome shaped bottom. In some aspects, the system includes where the plunger and the sample processing well are configured such that, upon complete insertion of the plunger into the sample processing well, the nub contacts the bottom of the sample processing well. In some aspects, the system includes where the plurality of flutes extend from the closed rounded tip less than the entire length of the elongated hollow cone structure. In some aspects, the system includes where the plurality of flutes extend from the closed rounded tip less than half the entire length of the elongated hollow cone structure. In some aspects, the system includes where the sample processing well comprises a mid-well flare in the sample processing well diameter that segments the sample processing well into a top volume and a bottom volume having different nominal diameters. In some aspects, the system includes where the nominal diameter of the bottom volume is essentially equal to the maximum diameter of the fluted portion of the plunger. In some aspects, the system includes where the nominal diameter of the top volume is greater than the maximum diameter of the fluted portion of the plunger. In some aspects, the system includes where the nominal diameter of the top volume is at least 1.1 times greater than the maximum diameter of the fluted portion of the plunger. In certain embodiments, when the plunger is inserted completely into the sample processing well the plurality of flutes do not extend to the level of the top volume. In certain embodiments, when the plunger is inserted completely into the sample processing well the plurality of flutes extend from the closed rounded tip essentially to the level of the mid-well flare. In some aspects, the system includes where the mid-well flare comprises 50% or less of the length of the sample processing well. In some aspects, the system includes where the sample processing well and the plunger are configured such that, upon insertion of the plunger into the sample processing well, sample processing buffer does not rise above the mid-well flare. In some aspects, the system includes where the sample processing well is an elution well and upon complete insertion of the plunger into the elution well the empty volume enclosed by the elution well and the plurality of flutes does not exceed the elution well buffer volume. In some aspects, the system includes where the elution well buffer volume is between 10 µl and 100 µl. In some aspects, the system includes where the sample processing well is contained in a sample processing cartridge. In some aspects, the system includes where the system comprises a plurality of plungers and the sample processing cartridge includes a plurality of sample processing wells equal to or greater than the number of plungers. In some aspects, the system includes where the number of plungers and number of sample processing wells are three or more. In some aspects, the system includes a plurality of sample processing cartridges each comprising a plurality of sample processing wells and a plurality of plungers equal to or less than the total number of sample processing wells of the system. In some aspects, the system includes where a plunger manipulator configured to physically manipulate the plunger in at least a vertical direction. In some aspects, the system includes where the plunger manipulator comprises a plunger grasping mechanism including where the plunger manipulator is a plunger bar. In some aspects, the system includes where the plunger bar includes a plurality of plunger grasping mechanisms corresponding to the number of plungers of the system. In some aspects, the system includes a plunger magnet configured to be inserted through the open top of the plunger. In some aspects, the system includes a plunger magnet manipulator attached to the plunger magnet and configured to physically manipulate the plunger magnet in at least a vertical direction. In some aspects, the system includes where the plunger magnet manipulator is a plunger magnet bar comprising a plurality of plunger magnets equal to the number of plungers of the system. In some aspects, the system includes where the plunger manipulator is configured to be translated in at least one horizontal direction. In some aspects, the system includes where the plunger magnet manipulator is configured to be translated in at least one horizontal direction. In some aspects, the system includes where the sample processing cartridge comprises at least one additional processing well adjacent to each sample processing well and the horizontal translation of the plunger manipulator is configured to allow movement of each plunger from an additional processing well to or from a sample processing well. In some aspects, the system includes where the horizontal translation of the plunger magnet manipulator is coincident with the horizontal translation of the plunger manipulator. In some aspects, the system includes where the plunger manipulator and the plunger magnet manipulator are physically linked.

Aspects of the instant disclosure include a method of eluting nucleic acid from attached magnetic particles by: a) inserting into an elution well comprising an elution buffer a magnetized plunger comprising magnetically attached magnetic particles comprising attached nucleic acid; b) driving the magnetized plunger to the bottom of the elution well to center the magnetized plunger in the elution well; c) retracting a magnet out of the plunger to demagnetize the plunger; d) reciprocating the demagnetized plunger up and down in the elution buffer at a first vertical speed sufficient to elute the nucleic acid; and e) removing the plunger from the elution buffer at a second vertical speed, wherein the second vertical speed is slower than the first vertical speed.

In some aspects, the method includes two or more steps of driving the demagnetized plunger to the bottom of the elution well to center the demagnetized plunger in the elution well. In some aspects, the method includes where the driving the demagnetized plunger to the bottom of the elution well to center the demagnetized plunger in the elution well is performed at a third vertical speed that is faster than both the first and second vertical speeds. In some aspects, the method includes one or more mixing steps comprising reciprocating the plunger sufficient to mix the elution buffer prior to removing the plunger. In some aspects, the method includes where at least one of the one or more mixing steps comprises a pause of the plunger in the elution buffer. In some aspects, the method includes where during the pause the magnet is inserted into the plunger for a period of time sufficient to allow the magnetic particles to reattach to the remagnetized plunger and then the magnet is removed from the plunger to allow the magnetic particles to disassociate from the plunger into the elution buffer. In some aspects, the method includes where, following elution of the nucleic acid and removal of the plunger, the nucleic acid containing elution buffer is removed. In some aspects, the method includes where removal of the nucleic acid containing elution buffer is performed by pipetting. In some aspects, the method includes where the volume of elution buffer is between 10 µl and 300 µl.

BRIEF DESCRIPTION OF THE FIGURES

FIGS. 13A-13C shows three sets of four plungers affixed to a plunger bar and three sets of four magnets affixed to a magnet bar according to one embodiment of the instant disclosure. FIG. 13A depicts an 'up' position, wherein the magnets clear the plungers, and the plungers clear the wells. FIG. 13B depicts a 'down' position, wherein the magnets reach the plunger bottoms (as shown in FIG. 13C), and the plungers reach the bottoms of each well.

DEFINITIONS

Figure 1A:
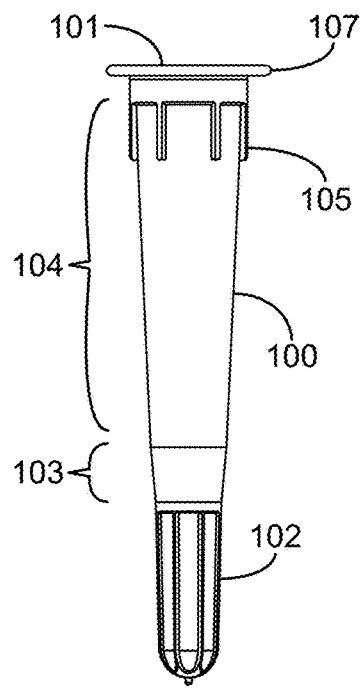
FIGS. 1A-1C provide various views of one embodiment of a plunger according to the instant disclosure.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the identity of" includes determining the most likely identity of a particular compound or formulation or substance, and/or determining whether a predicted compound or formulation or substance is present or absent. "Assessing the quality of" includes making a qualitative or quantitative assessment of quality e.g., through the comparisons of a determined value to a reference or standard of known quality.

The term "bodily fluid" as used herein generally refers to fluids derived from a "biological sample" which encompasses a variety of sample types obtained from an individual or a population of individuals and can be used in a diagnostic, monitoring or screening assay. The definition encompasses blood and other liquid samples of biological origin. The definition also includes samples that have been manipulated in any way after their procurement, such as by mixing or pooling of individual samples, treatment with reagents, solubilization, or enrichment for certain components, such as nucleated cells, non-nucleated cells, pathogens, etc.

The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like.

The term "magnetizable", as used herein, describes a component of the device that is sufficiently configured such that a magnetic field may propagate through it whether the magnetic field is generated in the component itself or applied from an outside source or separate component. For example, in some instances a component may be magnetizable when the component itself does not generate a magnetic field but a magnetic field, e.g., as applied by an external magnet, is positioned sufficiently close to or within the component such that the magnetic field propagates through the component. A magnetized component may therefore be the component to which magnetic particles attach, e.g., by generating a magnetic field in the component or by passing a magnetic field through the component, e.g., by placing a magnet within the component. As such, the magnetization of a particular component may encompass the joining of a non-magnetic component, e.g., a non-magnetic plunger, with a magnetic component, e.g., a magnetic bar, in sufficient arrangement such that the magnetic field of the magnetic component passes through the non-magnetic component. A magnetizable component, in some instances, may also be electrically magnetizable, e.g., through the use of a toggle-able electromagnet.

The term "elution well", as used herein, generally refers to a depression that contains elution buffer. Such an elution well may be present in a sample processing cartridge or any other compatible device capable being used in the methods as described herein. In some instances, an elution well may be the inner portion of an elution tube and, as such, in some instances, the terms "elution well" and "elution tube" may be used interchangeably. However, an ordinary skilled artisan will readily understand where an elution tube, being an independent vessel configured to contain elution buffer, and an elution well, which frequently refers to a well within a processing cartridge, may or may not be appropriately substituted for one another.

DETAILED DESCRIPTION

This instant disclosure provides methods of processing a sample in an automated sample processing device including devices configured for the automated extraction or isolation of nucleic acids. Also provided are plungers for use in such devices and methods of sample processing. Systems for performing the described methods and employing the described plungers are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The instant disclosure provides methods of processing a sample in an automated processing device. Aspects of the method generally relate to processes involved in the processing of cellular samples for the isolation and/or extraction of nucleic acids derived from the cells of the cellular sample and/or other organisms (e.g., pathogenic organisms) or biological contaminates present in the sample. Processes involved in nucleic acid isolation/extraction may include but are not limited to lysis (e.g., lysing the cells of the cellular sample), elution (i.e., eluting the nucleic acid extracted from the cells of the cellular sample) and washing (e.g., washing the nucleic acid in the lysed sample, washing the eluted nucleic acid, etc.). Nucleic acids may be extracted or isolated for various purposes including but not limited to use in making an assessment e.g., a diagnostic or clinical assessment e.g., as determined by an assay including e.g., a nucleic acid amplification assay.

In certain aspects, the sample is a biological sample including but not limited to e.g., a sample derived from a bodily fluid including e.g., a bodily fluid of a human. In some instances, the sample is a cellular sample. A cellular sample is a collection cells, e.g., from whole blood, serum, plasma, a tissue, organ, and/or the like of a mammal (e.g., a human, a rodent (e.g., a mouse), or any other mammal of interest). In other aspects, the cellular sample is a collection cells from a source other than a mammal, such as bacteria, yeast, insects (e.g., *drosophila*), amphibians (e.g., frogs (e.g., *Xenopus*)), viruses, plants, or any other non-mammalian nucleic acid sample source.

Methods of the instant disclosure may include one or more lysis steps. Lysis of cells and/or organisms of a sample will generally include physical lysis steps (i.e., mechanical lysis), chemical lysis steps, enzymatic lysis steps or a combination thereof. Physical lysis steps, chemical lysis steps and enzymatic lysis steps may be performed coincidently or may be performed in groups or individually in succession.

Chemical lysis may include incubating a sample in one or more chemical lysis agents for a period of time sufficient for release of the nucleic acid from the cells and/or organisms of the sample. As particular cells and organisms are more or less resistant to chemical lysis the duration chemical lysis and the particular chemical lysis agents used will vary depending at least in part on the cells and/or organisms of the sample. Chemical lysis agents useful in lysing a variety of different cells and/or organisms include but are not limited to e.g., surfactants/detergents (e.g., SDS (sodium dodecylsulfate), Sodium Deoxycholate, CTAB (cetyltrimethylammonium bromide), NP-40 (nonyl phenoxypolyethoxyl ethanol), Nonidet P-40 (octylphenoxy polyethoxyethanol), Triton X-100, Polysorbate 20 (Tween 20, Polyoxyethylene (20) sorbitan monolaurate), etc.), chaotropes (e.g., sodium iodide, guanidine HCl, guanidine isothiocyanate, urea, etc.), thiol reduction agents (2-Mercaptoethanol (beta-mercaptoethanol (BME)), 2-Mercaptoethylamine-HCl, Tris (2-carboxyethyl) phosphine hydrochloride (TCEP), cysteine hydrochloride, dithiothreitol (DTT), etc.), and the like. Such chemical lysis agents may be contained, either alone or in combination with other agents, in a lysis buffer.

Enzymatic lysis may include incubating a sample in one or more enzymatic lysis agents (i.e., lysis enzymes) for a period of time sufficient for release of the nucleic acid from the cells and/or organisms of the sample. As particular cells and organisms are more or less resistant to enzymatic lysis the duration enzymatic lysis and the particular enzymatic lysis agents used will vary depending at least in part on the cells and/or organisms of the sample. Enzymatic lysis agents useful in lysing a variety of different cells and/or organisms include but are not limited to e.g., Achromopeptidase enzymes, a-Hemolysin enzymes, Cellulase enzymes, Collagenase enzymes, DNase enzymes, Elastase enzymes, Hyaluronidase enzymes, Labiase enzymes, Lysostaphin enzymes, Lysozyme enzymes, Lyticase enzymes, Mutanolysin enzymes, Papain enzymes, Pectinase enzymes, Pectolyase enzymes, Protease Type XIV enzymes, Streptolysin O enzymes, Tetanolysin enzymes, Trypsin enzymes, and the like. Such enzymatic lysis agents may be contained, either alone or in combination with other agents, in a lysis buffer.

Lysis buffers may or may not include additives including e.g., agents for the inactivation of cellular nucleases. In some instances, agents utilized for lysing cells or organisms may include additional functions desirable in nucleic acid extraction, including e.g., inactivation of cellular nuclease functions, such as e.g., chaotropes, etc.

Physical (i.e., mechanical) lysis steps of the instant methods may include a single mechanical lysis method or a combination of different mechanical lysis methods. Any convenient method of mechanical lysis may be employed in the instantly described methods provided the method is compatible with the devices and vessels employed and is sufficient to lyse the cells and/or organism of the sample.

Mechanical lysis methods vary greatly but generally include mixing and/or agitating the sample to disrupt the cell membranes and/or cell walls of the cells and/or organisms of the sample. Mechanical lysis may be employed with or without agitation components or devices added to the sample including but not limited to e.g., a stir bar, beads, homogenizers, etc. In some instances, agitation is performed by shaking or swirling the entire vessel. In other instances, agitation is performed by holding the vessel stationary and agitating an agitation component or device within the vessel.

In some instances, a plunger as described herein may find use as an agitation component. Use of a plunger as an agitation component is not limited to agitation during a lysis step and may include e.g., agitation during any other step of processing including but not limited to e.g., agitation during a mixing step, agitation during a washing step, agitation during an elution step, etc.

A plunger may find use, e.g., for mixing fluids present in the wells of a sample processing cartridge, providing a surface onto which magnetic particles may be captured, e.g., during an elution step as described in more detail herein. A magnetizable plunger may also find use in moving nucleic acid attached to the magnetic particles through various steps of a process where e.g., the magnetic particles may be moved successively through wells of a sample processing cartridge for washing of nucleic acids present on the magnetic particles. As described in more detail herein, the plunger may have a shape that fills or nearly fills the volume of the bottom portion of one or more wells of a sample processing cartridge, including e.g., the elution well. In some instances, the relationship between the size of the closed end of the plunger and the bottom of a sample processing well forces fluid in the well to be driven up and down, during vertical reciprocating of the plunger, with a range large enough to adequately mix reagents therein (e.g., to wash, elute, etc.) and/or nucleic acids present on magnetic particles.

Methods of the instant disclosure may include one or more elution steps for the efficient elution of nucleic acid from a sample, including e.g., a lysed sample containing lysed cells, lysed tissue, lysed organisms, or a combination thereof. Elution of nucleic acid will generally involve extraction of the nucleic acid from a solution or solid support. For example, in some instances, nucleic acid may be eluted from magnetic particles to which the nucleic acid is attached.

During an elution step nucleic acid may be dissolved into an elution buffer suitable for dissolving nucleic acids. Useful elution buffers will vary depending on the particular context of elution and may include but are not limited to e.g., water, tris buffer, tris-EDTA buffer (TE), phosphate buffered saline (PBS), tris buffered saline (TBE), and the like. In some instances, an elution buffer may be used that is specific for downstream applications of the eluted nucleic acid, e.g., in some instances, the elution buffer may exclude one or more components that may interfere with PCR including but not limited to e.g., ethylenediaminetetraacetic acid (EDTA).

The volume of the elution buffer into which the nucleic acid is to be dissolved may vary depending e.g., the size of downstream reaction vessels (including but not limited to e.g., PCR reaction vessels, etc.), the expected amount of nucleic acid to be extracted from the sample, the desired reaction volume of downstream assays, etc. In some instances, the amount of elution buffer, e.g., as used in an elution well of a sample processing device, may range from 10 µl or less to 500 µl or more including but not limited to e.g., 10 µl to 300 µl, 15 µl to 300 µl, 20 µl to 300 µl, 25 µl to 300 µl, 30 µl to 300 µl, 35 µl to 300 µl, 10 µl to 200 µl, 15 µl to 200 µl, 20 µl to 200 µl, 25 µl to 200 µl, 30 µl to 200 µl, 35 µl to 200 µl, 10 µl to 150 µl, 15 µl to 150 µl, 20 µl to 150 µl, 25 µl to 150 µl, 30 µl to 150 µl, 35 µl to 150 µl, 10 µl to 100 µl, 15 µl to 100 µl, 20 µl to 100 µl, 25 µl to 100 µl, 30 µl to 100 µl, 35 µl to 100 µl, 10 µl to 75 µl, 15 µl to 75 µl, 20 µl to 75 µl, 25 µl to 75 µl, 30 µl to 75 µl, 35 µl to 75 µl, 10 µl to 50 µl, 15 µl to 50 µl, 20 µl to 50 µl, 25 µl to 50 µl, 30 µl to 50 µl, 35 µl to 50 µl, 10 µl to 45 µl, 15 µl to 45 µl, 20 µl to 45 µl, 25 µl to 45 µl, 30 µl to 45 µl, 35 µl to 45 µl, 10 µl to 40 µl, 15 µl to 40 µl, 20 µl to 40 µl, 25 µl to 40 µl, 30 µl to 40 µl, 35 µl to 40 µl, 10 µl to 35 µl, 15 µl to 35 µl, 20 µl to 35 µl, 25 µl to 35 µl, 30 µl to 35 µl, 10 µl to 30 µl, 15 µl to 30 µl, 20 µl to 30 µl, 25 µl to 30 µl, 20 µl, 25 µl, 30 µl, 35 µl, etc.

In some instances, methods of the instant disclosure and/or devices of the instant disclosure may include or be configured to be adaptable with a reaction vessel system and/or a method of using a reaction vessel system and/or components of a reaction vessel system as described in e.g., which claims priority to U.S. Ser. No. 62/308,620, the disclosures of which are incorporated herein by reference in their entireties.

In some instances, components of the devices and systems as described herein may be specifically designed for use with a particular volume of elution buffer or range of elution buffer volume. In certain instances, such design with or without the methods described herein may reduce one or more undesirable outcome of solution manipulation. Undesirable outcomes of solution manipulation include but are not limited to e.g., aeration of the solution, formation of air pockets in the solution and/or processing well, spillage of the solution outside of the processing well, excessive evaporation of the solution, etc. In some instances, undesirable outcomes of solution manipulation include outcomes pertaining to particles, e.g., magnetic particles within the solution, including but are not limited to e.g., inadequate release of particles into the solution, inadequate mixing of particles in the solution, buildup of particles on a surface of the preparation well, buildup of particles on a surface of an agitation component (e.g., a plunger), and the like.

Methods of the instant disclosure include methods of efficient elution of nucleic acid from attached magnetic particles wherein the methods include a series of actions of a magnetizable agitator including e.g., a magnetizable plunger as described herein. Such methods may provide certain benefits including but not limited to the prevention or reduction of one or more undesirable outcomes of solution manipulation.

Such methods may include performing steps of a method at particular speeds wherein the speeds may be determined relative to other speeds of the method. In certain instances, speeds of interest relate to vertical movements of a plunger. In certain instances, speeds of interest relate to vertical movements of a magnet. In certain instances, speeds of interest relate to vertical movements of a plunger/magnet pair (i.e., when a magnet is disposed inside of a hollow plunger). Where one speed is described as faster than another, the faster speed takes a shorter period of time to complete a vertical movement (e.g., a movement from an upper position to a lower position, a movement from a lower position to an upper position, a cycle from one position to an upper or lower position and returning to the original position, etc.) as compared to the corresponding movement in the slower speed. The two compared speed need not necessarily complete the same movements and differing movements may be compared as faster or slower to one another based on a portion of a movement, e.g., where portions of the two movements correspond e.g., in part of the upward motion, in part of the downward motion, etc.

In certain embodiments, a method for elution of nucleic acid from attached magnetic particles may include movement of a magnetized plunger into an eluate well. Such movements may include driving the magnetized plunger to the bottom of the elution tube with sufficient force such that the corresponding geometry between the plunger and the bottom of the elution tube center the plunger in the center of the elution tube. In some instances, the driving force serves other purposes, e.g., to drive air (e.g., air pockets) out of the elution well, to cause liquid to rise uniformly around all sides of the plunger, to cause liquid to rise uniformly around all sides of the elution well, etc.

In certain embodiments, a method for elution of nucleic acid from attached magnetic particles may include movement of the magnet out of the magnetized plunger, releasing magnetized particles magnetically bound to the plunger into the elution buffer. In some instances, following such movement of the magnet out of the plunger, the elution buffer may be mixed, e.g., by reciprocating the plunger up and down vertically. Such mixing may be performed slowly, e.g., as compared to other vertical movements of the method, and may perform various functions including but not limited to e.g., washing particles off the sides of the plunger, washing particles off the sides of the elution well, forcing air out of the elution well, etc. In some instances, the mixing may be repeated two or more times including but not limited to e.g., where the mixing is repeated for two or more cycles, three or more cycles, four or more cycles, five or more cycles, six or more cycles, seven or more cycles, eight or more cycles, nine or more cycles, ten or more cycles, etc.

In certain embodiments, a method for elution of nucleic acid from attached magnetic particles may include movement of the demagnetized plunger (i.e., the plunger without the magnetic bar inserted into the hollow cavity of the plunger) into the eluate well. Such movements may include driving the demagnetized plunger to the bottom of the elution tube with sufficient force such that the corresponding geometry between the plunger and the bottom of the elution tube center the plunger in the center of the elution tube. In some instances, the driving force serves other purposes, e.g., to drive air (e.g., air pockets) out of the elution well, to cause liquid to rise uniformly around all sides of the plunger, to cause liquid to rise uniformly around all sides of the elution well, etc.

In certain embodiments, a method for elution of nucleic acid from attached magnetic particles may include one or more mixing movements. In some instances, mixing movements include quick, as compared to other movements of the method, movement of the magnet into the plunger that has already been driven to the bottom of the elution well or tube. Such quick movements of the magnet into the plunger that is already at the bottom of the elution tube may server various purposes including but not limited to e.g., to ensure that particles are preferentially attracted to the bottom of the plunger as compared to the upper portions of the plunger, i.e., particles are not substantially attracted to the early magnet movement to allow the accumulation of particles at the top of the elution liquid.

In some instances, mixing movements include quickly moving the magnet out of the plunger while the plunger remains at the bottom of the elution well. Such a movement may serve various functions including but not limited to e.g., to preferentially keep particles at the bottom of the elution well, i.e., to prevent particles from being attracted to the upper portions of the plunger and/or the surface of the elution buffer.

In some instances, mixing movements include reciprocating the demagnetized plunger vertically up and down in the elution buffer. In some instances, such mixing may be performed at a speed and for a duration sufficient to homogenize the elution buffer (e.g., place the magnetic particles in homogenous suspension). In some instances, such mixing may be performed at a speed and for a duration sufficient to minimize aggregation of the particles at the surface of the elution buffer.

In some instances, mixing movements include moving the demagnetized plunger to the bottom of the elution tube following other mixing movements. Such post-mixing movements of the plunger to the bottom of the elution tube may serve various purposes including but not limited to e.g., to ensure the sides of the elution tube are sufficiently washed by the elution buffer up to a height corresponding to the maximum level of elution buffer rise during the mixing, position the plunger appropriately for the next movement of the method, etc.

In some instances, the mixing steps or combinations thereof may be repeated two or more times including but not limited to e.g., where the mixing step or a combination thereof is repeated for two or more cycles, three or more cycles, four or more cycles, five or more cycles, six or more cycles, seven or more cycles, eight or more cycles, nine or more cycles, ten or more cycles, five to ten cycles, six to ten cycles, seven to ten cycles, four to nine cycles, four to eight cycles, four to six cycles, etc.

In some instances, a set of mixing steps (i.e., a set of mixing motions) may be configured to be contained within a particular time duration. For example in some instances, a set of mixing steps may be configured to take a set time period ranging from less than one minute to more than ten minutes including but not limited to e.g., 0.25 min. to 3 min., 0.5 min. to 3 min., 0.75 min. to 3 min., 1 min. to 3 min., 0.5 min. to 2 min., 1 min. to 2 min., 0.5 min. to 5 min., 0.5 min to 10 min., 0.25 min., 0.5 min., 0.75 min., 1 min., 1.25 min., 1.5 min., 1.75 min., 2 min., 2.5 min., 3 min., 3.5 min., 4 min., 5 min., 6 min., 7 min., 8 min., 9 min., 10 min., etc. In some instances, the use of a set time period allows the addition or subtraction of washing cycles in a convenient temporal increment.

In some instances, movements, including mixing movements, include one or more pausing steps. Pausing steps may serve various purposes in the described method including but not limited to e.g., allowing particles to be attracted to the magnetized plunger including e.g., where such attracting draws particles away from the surface of the elution buffer. In some instances, one or more pausing steps may be inserted between plunger movements as described herein. In some instances, one or more pausing steps may be inserted between magnet movements as described herein. In some instances, one or more pausing steps may be inserted between magnet movements and plunger movements as described herein. In some instances, one or more pausing steps may be inserted between plunger movements and magnet movements as described herein.

In certain embodiments, a method for elution of nucleic acid from attached magnetic particles may include a final movement of the plunger out of the elution well, e.g., out of the elution buffer following sufficient elution. Such final movement of the plunger out of the elution well may be performed following all other movement steps, i.e., following sufficient elution of the nucleic acid into the elution buffer. Removal of the plunger from the elution well and elution buffer may place the system in proper positioning for a next step in a downstream process (including e.g., further processing of the eluted nucleic acid, analysis of the eluted nucleic acid, amplification of the eluted nucleic acid, etc.).

In some instances, following elution of a nucleic acid as described herein, the eluted nucleic acid may be subjected to amplification and analysis or processed using amplification and analysis devices or components thereof as described in e.g., which claims priority to U.S. Ser. No. 62/308,632, the disclosures of which are incorporated herein by reference in their entireties.

In some instances, the removal of the plunger is performed slowly, e.g., as compared to other vertical movements of the method, including e.g., where the plunger removal movement is the slowest of the vertical movements of the method. Slow removal of the plunger may serve various purposes including but not limited to e.g., preventing or reducing removal of elution buffer by preventing or reducing the amount of liquid adhered to the plunger.

Methods of the instant disclosure may further include movements of components associated with parallel processing of multiple samples, including but not limited to coordinated and/or synchronized vertical movements of a plurality of plunger, a plurality of magnets, a plurality of sample processing cartridges, etc. For example, in some instances, the methods may include components configured for the simultaneous movement of a plurality of plungers including e.g., a plunger manipulator configured to simultaneously move a plurality of plungers, e.g., a plunger bar. In some instances, the methods may include components configured for the simultaneous movement of a plurality of plunger magnets including e.g., a plunger magnet manipulator configured to simultaneously move a plurality of plunger magnets, e.g., a plunger magnet bar.

In some instances, methods of the instant disclosure and/or devices of the instant disclosure may include or be configured to be adaptable with a multi-assay processing and analysis system and/or a method of multi-assay processing and analysis as described in e.g., which claims priority to U.S. Ser. No. 62/308,625, the disclosures of which are incorporated herein by reference in their entireties.

In some instances, methods of the instant disclosure may include horizontal movements, e.g., translation movements, associated with the processing of a sample through a series of different processing step. Such processing steps may be coordinated into the design of a sample processing cartridge comprising a plurality of sample processing wells, including but not limited to sample processing wells in addition to an elution well. The plurality of sample processing wells may be arranged in any convenient relative orientation including e.g., where wells corresponding to successive steps are arrange in linearly adjacent wells.

In some instances, methods of the instant disclosure and/or devices of the instant disclosure may include a sample preparation cartridge and/or method of using a sample preparation cartridge and/or components of a system associated with a sample preparation cartridge as described in e.g., which claims priority to U.S. Ser. No. 62/308,618, the disclosures of which are incorporated herein by reference in their entireties.

Any liquid aspirating and dispensing steps described herein, including e.g., the movement of liquid between wells of a multi-well sample processing cartridge, may be performed using a pipettor, e.g., a robotic pipettor, such as a robotic pipettor of an automated sample preparation system.

In some instances, e.g., where nucleic acid attached magnetic particles are transferred between wells of a multi-well sample processing cartridge, the magnetizable plunger may also be used for such transferring and may be referred to as part of a magnetic particle transfer component.

A magnetic particle transfer component may include a plunger magnet bar suspended above one or more sample preparation units, and a magnetic rod for each plurality of linearly arranged wells (e.g., of a sample processing cartridge), the magnetic rod(s) attached to the plunger magnet bar and projecting from the plunger magnet bar toward the plurality of linearly arranged wells. The magnetic particle transfer component may further include a plunger bar suspended above the one or more sample preparation units, the plunger bar comprising a plunger attachment point for each plurality of linearly arranged wells, the plunger bar attachment point projecting from the plunger bar toward the plurality of linearly arranged wells. The plunger bar is at a position lower than the plunger magnet bar, such that the magnetic rods are positioned above their corresponding plungers and capable of being inserted into and removed from hollows of the plungers.

The magnetic particle transfer component further includes a horizontal translation drive for translating the plunger magnet bar (and accordingly, magnetic rods) and the plunger bar (and accordingly, plungers, when present) across the plurality of linearly arranged wells. The magnetic particle transfer component further includes a vertical magnetic rod and plunger bar translation drive for coupled vertical translation of the plunger magnet bar and the plunger bar, and a vertical magnetic rod translation drive for independent vertical translation of the plunger magnet bar (and accordingly, magnetic rods), for inserting and removing the magnetic rod into a plunger attached to the plunger bar at the plunger bar attachment point or plunger holder element.

According to certain embodiments, the plunger attachment point or plunger holder element is a fork that couples with complementary grooves or one or more flanges in an upper portion of the plunger.

The magnetic particle transfer component further includes a horizontal translation mechanism for translating the magnetic rod support structure (and accordingly, the magnetic rod(s)) and the plunger bar support structure across the plurality of linearly arranged wells. The magnetic particle transfer component further includes a vertical translation mechanism for vertically translating the magnetic rod(s) into/from the plunger(s) and a vertical translation mechanism for vertically translating the plunger bar(s)/plunger(s) into/from wells of the plurality of linearly arranged wells.

Devices and Systems

Aspects of the present disclosure provide a sample extraction and processing device. A sample extraction and processing device may be configured to carry out a method as described above. A device as described below comprises multiple components that are configured to function together in concert. In some instances, components of the subject device(s) and/or components attached to one or more of the subject devices may include components of a system for automated analysis and sample analysis systems as described in which claims priority to U.S. Ser. No. 62/308,617 and U.S. Ser. No. 62/357,772, the disclosures of which are incorporated herein by reference in their entireties.

Figure 9:
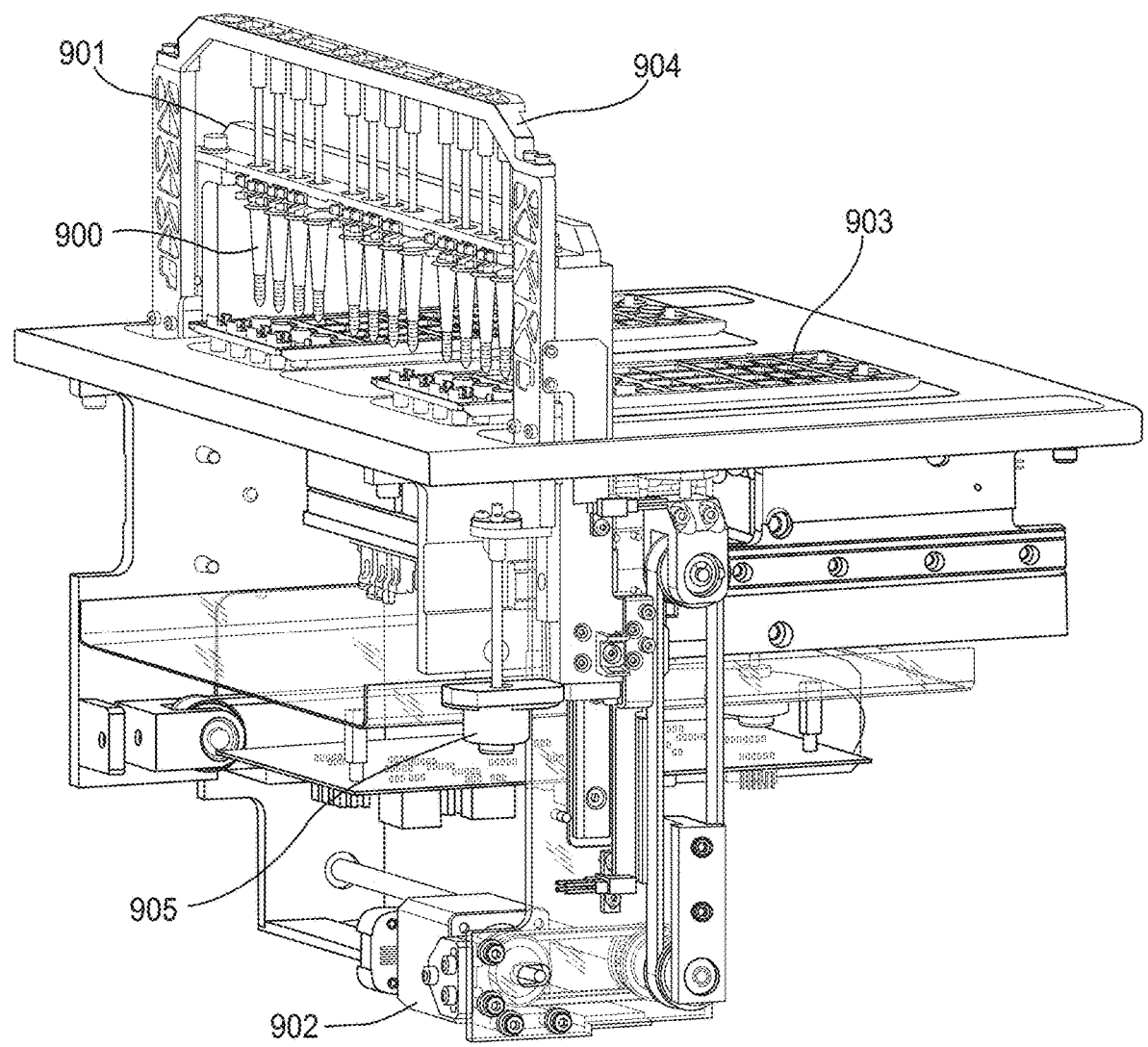
FIG. 9 shows three sets of four plungers affixed to a plunger bar and three sets of four magnets affixed to a magnet bar and other components according to one embodiment of the instant disclosure.
Figure 15:
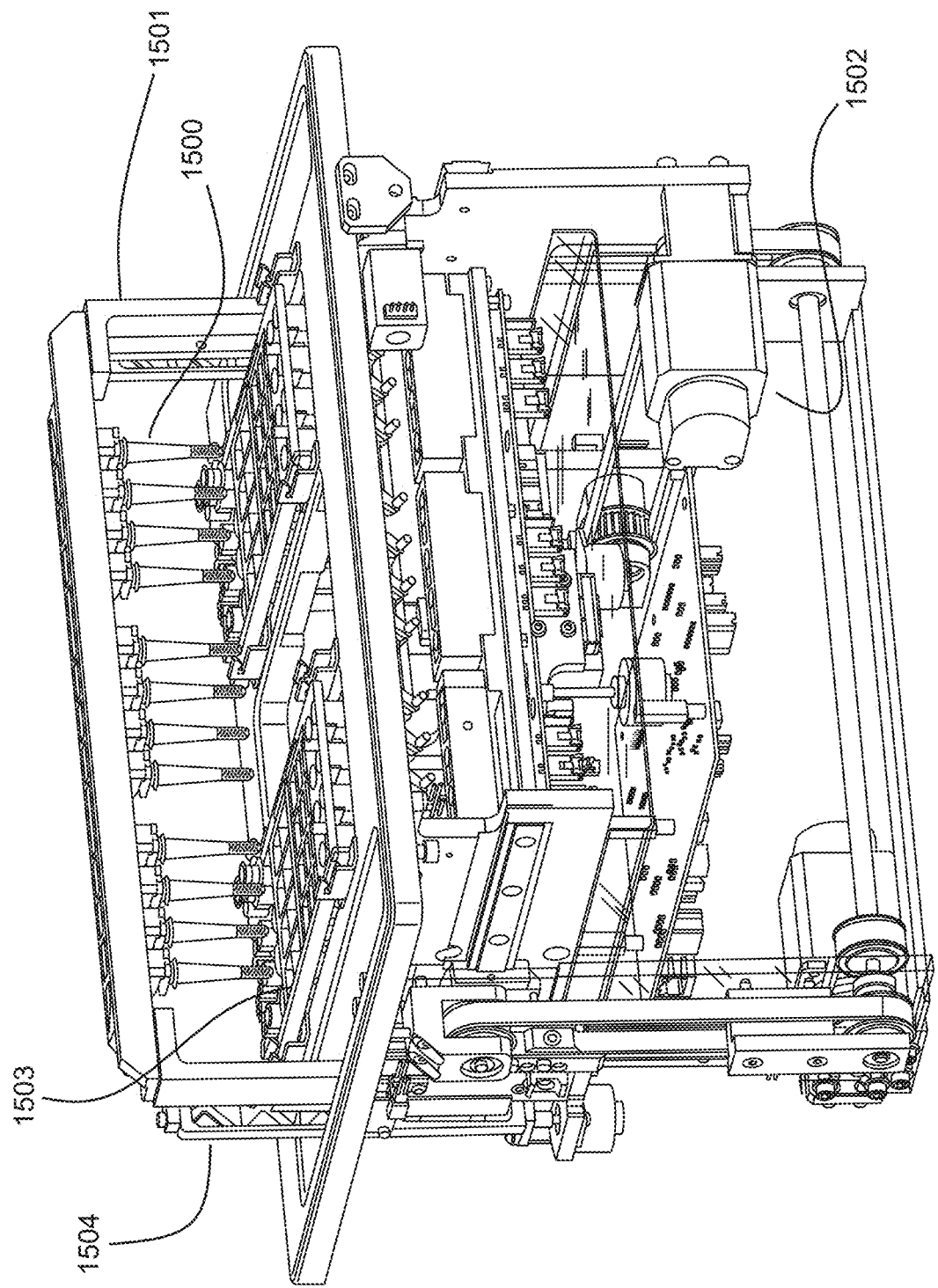
FIG. 15 shows three sets of four plungers affixed to a plunger bar and three sets of four magnets affixed to a magnet bar, where the magnets are inserted into the plungers, and the configuration includes horizontal translation components according to embodiments of the instant disclosure.

In one embodiment, FIG. 9 shows a sample extraction and processing device where a combination of motors or encoders and various components (as described below) drive automated sample extraction and processing (FIG. 15 provides an alternative view in which sample processing cartridges with linearly aligned processing wells can be seen beneath the hanging plungers with the magnets engaged).

For example, as depicted in FIG. 9, plungers (900) are connected to a plunger bar (901) which translates motion from a vertical drive motor (902) into movements utilized as described in the sample processing methods disclosed herein. For example, the vertical motions of the device raise and lower the plungers (900) into one or more wells of the sample processing cartridge (903) and the magnet bar (904)

driven by an actuator (905) controls the magnetization of the plungers by engaging or disengaging the magnets. FIG. 15 similarly depicts the plungers (1500), plunger bar (1501), vertical drive motor (1502), sample processing cartridges (1503) and the magnet bar (1504), however, as the magnets are engaged into the plungers, the magnet bar (1504) is largely behind the plunger bar (1501).

Plunger

An aspect of the present disclosure provides a plunger for use in a sample extraction and processing device of the present disclosure. For example, a plunger may be used when employing a unique set of plunger and plunger magnet motions which ensure the proper processing of magnetic microparticles that a sample (e.g., nucleic acid sample) may be bound to. A plunger may be made from any suitable materials that in general do not possess magnetic properties (i.e., materials that generally do not interfere with any magnetic fields). In some cases, a plunger may be made from an inert material such that the plunger does not chemically react or influence any chemical reactions with any materials that may be found within a processing well. In certain cases, the plunger material does not significantly weaken the strength of the plunger magnetic field, and a plunger magnetic field that radiates from a plunger magnet inserted into the plunger remains strong enough to attract magnetic microparticles. In some embodiments, a plunger may have a hydrophobic coating.

A plunger of the present disclosure may generally be of a shape similar to the shape of a processing well (e.g., an elution tube). In some cases, the distal end of the plunger may be tapered to fit the conical bottom of a processing well. In some instances, the distal tip of the plunger is V-shaped. In some instances, the distal tip of the plunger is U-shaped. In some embodiments, the shape of a plunger allows for a tight fit of the plunger within a processing well (see, FIG. 6).

Figure 6:
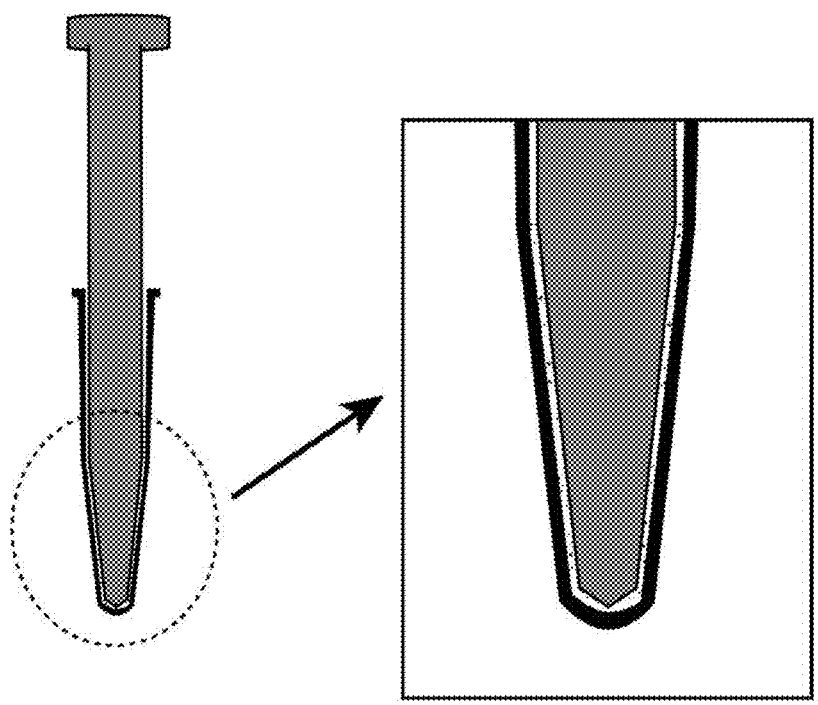
FIG. 6 shows a schematic of a plunger which has a molded fit with the shape and size of the elution tube.

A plunger with a taper at the closed end, e.g., a plunger with a V-shaped distal end or a plunger with a U-shaped distal end, may serve additional purposes including but not limited to e.g., to center the plunger within the processing well, to force any air pockets found within a processing well out, to causes any processing liquid to rise uniformly around all sides of the plunger, etc. FIG. 6, right panel, demonstrates the concept of centering a plunger at the bottom of a processing well where the processing liquid uniformly surrounds all sides of the plunger.

In some embodiments, a plunger is hollow except at one end (e.g., the 'distal end', the 'bottom end', or the 'closed end'). The hollow space in a plunger allows for a tight fit with a plunger magnet upon insertion. In some cases, the plunger comprises a mechanism wherein when a plunger magnet is inserted, the plunger and plunger magnet may or may not be locked together. For example, in some cases, the plunger and the plunger magnet are not locked together or do not lock together but are indirectly coupled through a plunger bar and a magnet bar that are attached to one another such that the plunger and the plunger magnet move in concert with one another. A plunger bar attached to a plunger magnet bar, as described in more detail herein, may be attached such that they move together in one or more horizontal directions but may be configured such that they move independently in a vertical direction. In yet other cases, a plunger and plunger magnet can be locked together but can be easily physically decoupled, e.g., by a reversible locking mechanism.

In some aspects, a plunger of the present disclosure may be disposable, i.e., is discarded after a single use. In other aspects, a plunger of the present disclosure may be re-usable. In such cases, a plunger may undergo additional wash steps in order to remove any and all traces of sample (e.g., nucleic acids) from the plunger.

Plunger configurations will vary. In some instances, a plunger may be essentially conical or be composed of an elongated conical structure wherein such structure is hollow as described (see e.g., FIGS. 1A and 2A).

Figure 2A:
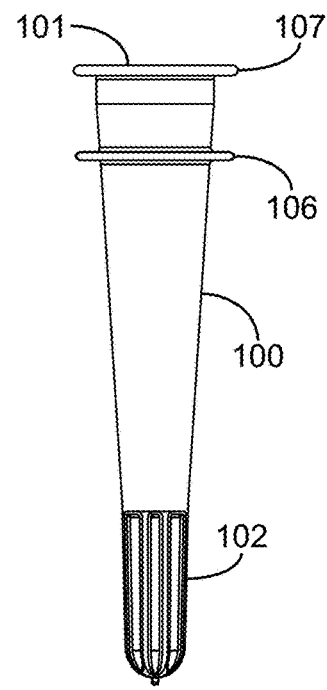
FIGS. 2A-2C provide various views of an alternative embodiment of a plunger according to the instant disclosure.

In certain embodiments, referring to FIGS. 1A and 2A, a plunger of the instant disclosure may include an elongated hollow clone structure (100) and a top opening (101). The plunger may include a plurality of flutes (102) at the closed end. In some instances, the plunger may further include two or more differing tapers, including e.g., a first taper (103) and a second taper (104) where the first taper is greater than the second taper. In other instances (e.g., FIG. 2A), the plunger may have essentially one taper. The plunger may also but does not necessarily include a stacking spacer where various staking spacers may find use including but not limited to e.g., raised ridges (105), a ring or lip or flange (106), or the like. In some instances, the plunger may include a plunger holder element (107) configured for interaction with a plunger manipulator or grabber as described herein.

Figure 1B:
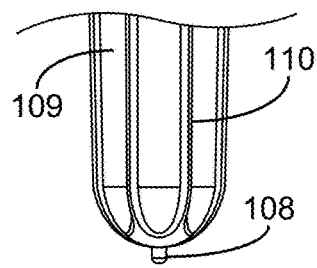
Figure 2B:
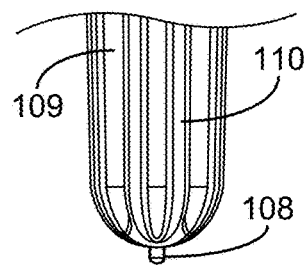

In certain embodiments, referring to FIGS. 1B and 2B, the closed end or 'tip' of the plunger may be rounded and may include an 'end nub' (108) at the most distal end. A flute (109) of the plunger tip is essentially a longitudinal groove in the plunger that may be defined by raised edges (110).

Figure 1C:
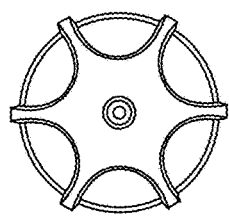
Figure 2C:
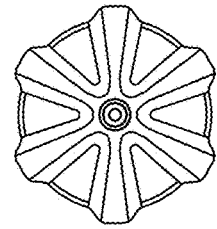

Referring to FIGS. 1C and 2C, the distance that the flutes extend to the closed end of the plunger will vary but, in certain embodiments will extend into the rounded tip but not to the end nub. The flute, being a groove in the plunger, will define a cavity which may, in some instances, be collectively defined for all flutes of the plurality as defining an empty volume of space. The volume of space ascribed to the flutes may be determined from the difference in volume of the plunger with and without the flutes (i.e., the difference between a plunger with the flutes and an identical plunger without the flutes). Such volume may or may not correspond to the volume of buffer used in one or more of the processing methods as describe herein. In some instances, the volume of the cavity defined by the flutes will be less than the volume of buffer used in one or more of the processing methods. In some instances, the volume of the cavity defined by the flutes will be more than the volume of buffer used in one or more of the processing methods.

Plungers of the instant disclosure may be configured to minimize contact of the plunger with the elution well. For example, in some instances, contact of a feature of the plunger with the elution well may generally prevent further contact of surfaces of plunger with the elution well. In some instances, contact of a nub feature of the plunger with the elution well may prevent further contact of surfaces of the plunger with the elution well. In some instances, contact of one or more flute features of the plunger with the elution well may prevent further contact of surfaces of the plunger with the elution well. In some instances, the general shape of the plunger, in relationship to the shape of the elution well, is configured to minimize contact between surfaces of the plunger with surfaces of the elution well, including but not limited to e.g., one or more tapers of the plunger, the contours of end of the plunger (e.g., contours of the rounded end of the plunger), etc. For example, in some instances, the plunger end and the bottom of the elution well are of sufficiently dissimilar shape so as to minimize contact of surfaces of the plunger with surfaces of the elution well.

Accordingly, the volume of the plurality of flutes will vary and may range from 10 mm$^3$ or less to 300 mm$^3$ or more including but not limited to e.g., between 10 mm$^3$ and 100 mm$^3$, between 15 mm$^3$ and 100 mm$^3$, between 20 mm$^3$ and 100 mm$^3$, between 25 mm$^3$ and 100 mm$^3$, between 10 mm$^3$ and 100 mm$^3$, between 10 mm$^3$ and 75 mm$^3$, between 15 mm$^3$ and 75 mm$^3$, between 20 mm$^3$ and 75 mm$^3$, between 25 mm$^3$ and 75 mm$^3$, between 10 mm$^3$ and 75 mm$^3$, between 10 mm$^3$ and 50 mm$^3$, between 15 mm$^3$ and 50 mm$^3$, between 20 mm$^3$ and 50 mm$^3$, between 25 mm$^3$ and 50 mm$^3$, between 10 mm$^3$ and 50 mm$^3$, between 10 mm$^3$ and 45 mm$^3$, between 10 mm$^3$ and 40 mm$^3$, between 10 mm$^3$ and 35 mm$^3$, between 15 mm$^3$ and 45 mm$^3$, between 20 mm$^3$ and 45 mm$^3$, between 20 mm$^3$ and 40 mm$^3$, between 20 mm$^3$ and 35 mm$^3$, between 25 mm$^3$ and 40 mm$^3$, between 25 mm$^3$ and 35 mm$^3$, 20 mm$^3$, 25 mm$^3$, 30 mm$^3$, 35 mm$^3$, 40 mm$^3$, 50 mm$^3$, 60 mm$^3$, 70 mm$^3$, 80 mm$^3$, 90 mm$^3$, 100 mm$^3$, etc.

Accordingly, in some instances the volume of the plurality of flutes will be configured to contain a volume of liquid where the volume of liquid will vary and may range from 10 μl or less to 300 μl or more including but not limited to e.g., between 10 μl and 100 μl, between 15 μl and 100 μl, between 20 μl and 100 μl, between 25 μl and 100 μl, between 10 μl and 100 μl, between 10 μl and 75 μl, between 15 μl and 75 μl, between 20 μl and 75 μl, between 25 μl and 75 μl, between 10 μl and 75 μl, between 10 μl and 50 μl, between 15 μl and 50 μl, between 20 μl and 50 μl, between 25 μl and 50 μl, between 10 μl and 50 μl, between 10 μl and 45 μl, between 10 μl and 40 μl, between 10 μl and 35 μl, between 15 μl and 45 μl, between 20 μl and 45 μl, between 20 μl and 40 μl, between 20 μl and 35 μl, between 25 μl and 40 μl, between 25 μl and 35 μl, 20 μl, 25 μl, 30 μl, 35 μl, 40 μl, 50 μl, 60 μl, 70 μl, 80 μl, 90 μl, 100 μl, etc.

The number of flutes will vary and may range from three to ten or more including but not limited to e.g., three to ten, three to nine, three to eight, three to seven, three to six, three to five, four to nine, four to eight, four to seven, four to six, five to nine, five to eight, five to seven, three, four, five, six, seven, eight, nine, ten, etc.

The wall thickness of plungers of the instant disclosure may vary and will generally be thin enough to allow insertion of a magnet into the hollow cavity of the plunger but thick enough to provide structural support. As such in some instances the nominal thickness of the plunger wall may range from 0.10 mm or less to 0.5 mm or more including but not limited to e.g., 0.15 mm to 0.45 mm, 0.2 to 0.45 mm, 0.25 to 0.45 mm, 0.3 to 0.45 mm, 0.15 mm to 0.40 mm, 0.15 mm to 0.35 mm, 0.15 mm to 0.30 mm, 0.15 mm to 0.25 mm, 0.20 mm to 0.40 mm, 0.25 mm, 0.35 mm, and the like.

Figure 3:
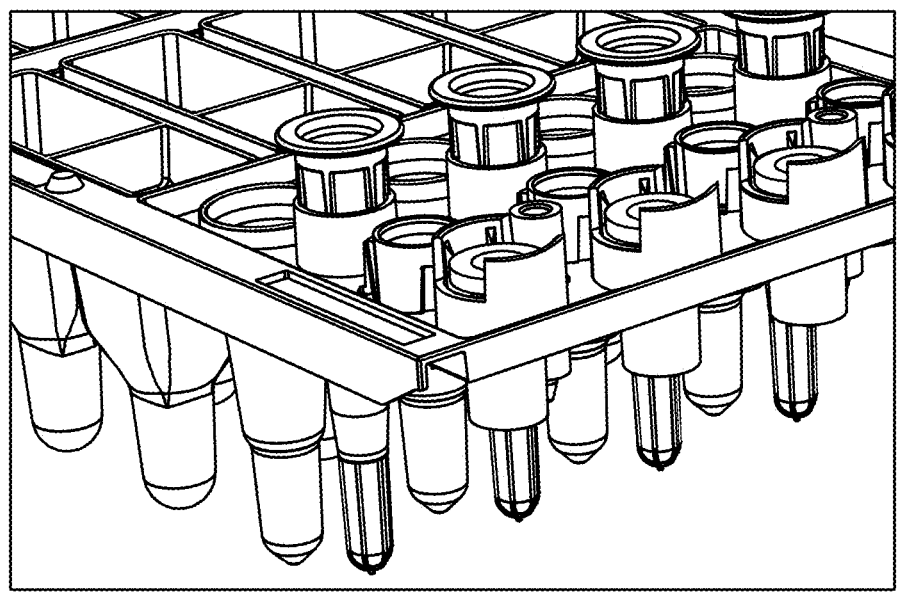
FIG. 3 provides a depiction of one embodiment of a plunger according to the instant disclosure resting in a sample processing cartridge as described herein.

Plungers of the instant disclosure may, in some instances, be provided in or configured to rest in a sample processing cartridge, including where a stacking element contacts the sample processing cartridge to position the plunger in a raised and accessible position (see e.g., FIG. 3). In some instances, the plunger stacking element will also facilitate the stacking of sample processing cartridge one on top of another, preventing the contact and/or dislodgement of vertically stacked plungers.

Plunger Bar

Aspects of this disclosure provide a plunger bar that comprises a mechanism to grasp onto a plunger, e.g., a plunger holder element. The plunger bar may be machined from any suitable materials that in general do not possess magnetic properties (i.e., materials that generally do not interfere with any magnetic fields). For example, a plunger bar may be machined from a bar of aluminum.

In some aspects, the plunger bar will comprise a grasping component that grasps onto a plunger. In some cases, the plunger bar will comprise more than one, more than two, more than three, more than four, more than five, more than six, more than seven, more than eight, more than ten, more than twelve, more than fourteen, more than sixteen, more than twenty individual grasping components that are capable of each grasping onto a plungers. In one embodiment, three sets of four grasping mechanisms are attached at precise locations on a plunger bar. In many cases, the positioning of the grasping components along the plunger bar is organized in such a way as to align the grasping components with the positioning of processing wells, and with the positioning of plunger magnets.

Figure 11:
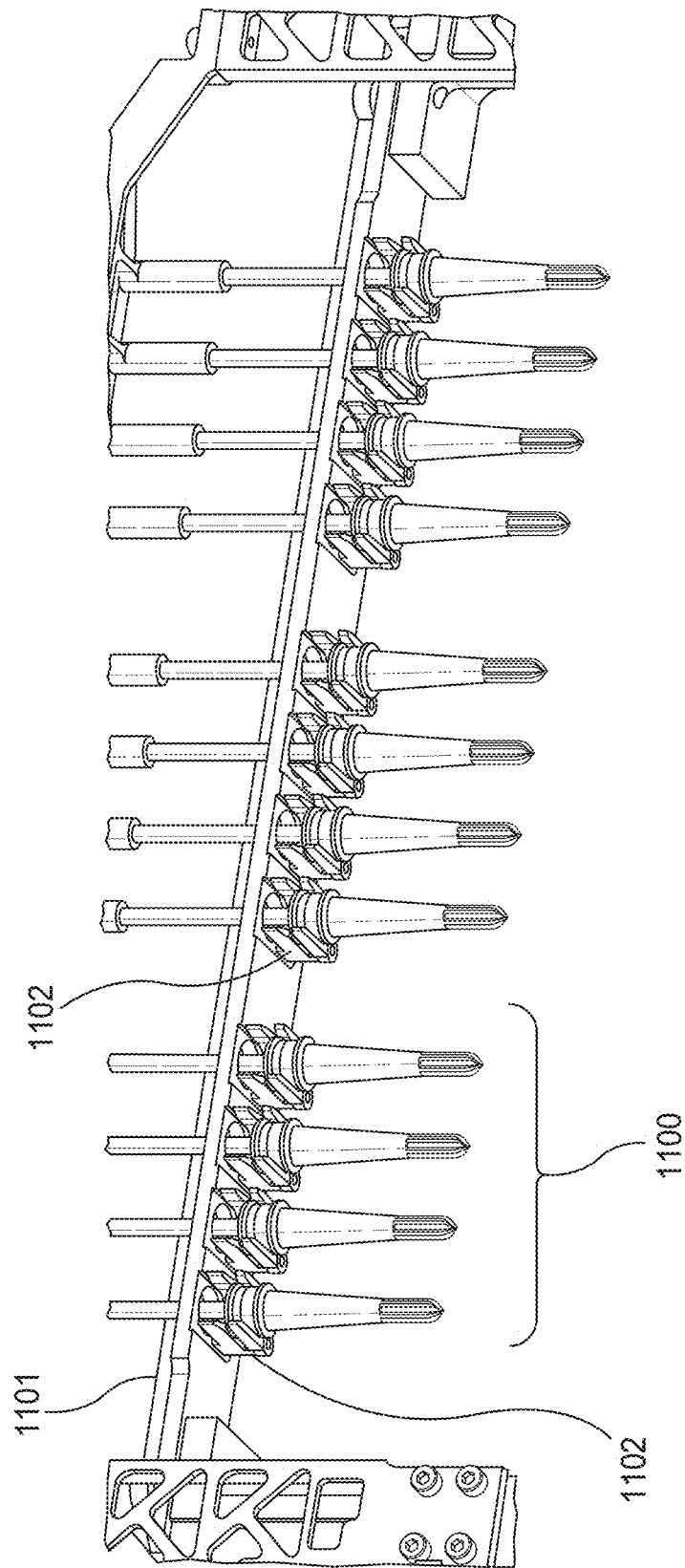
FIG. 11 shows three sets of four plungers affixed to a plunger bar and three sets of four magnets affixed to a magnet bar and other components according to one embodiment of the instant disclosure.
Figure 12:
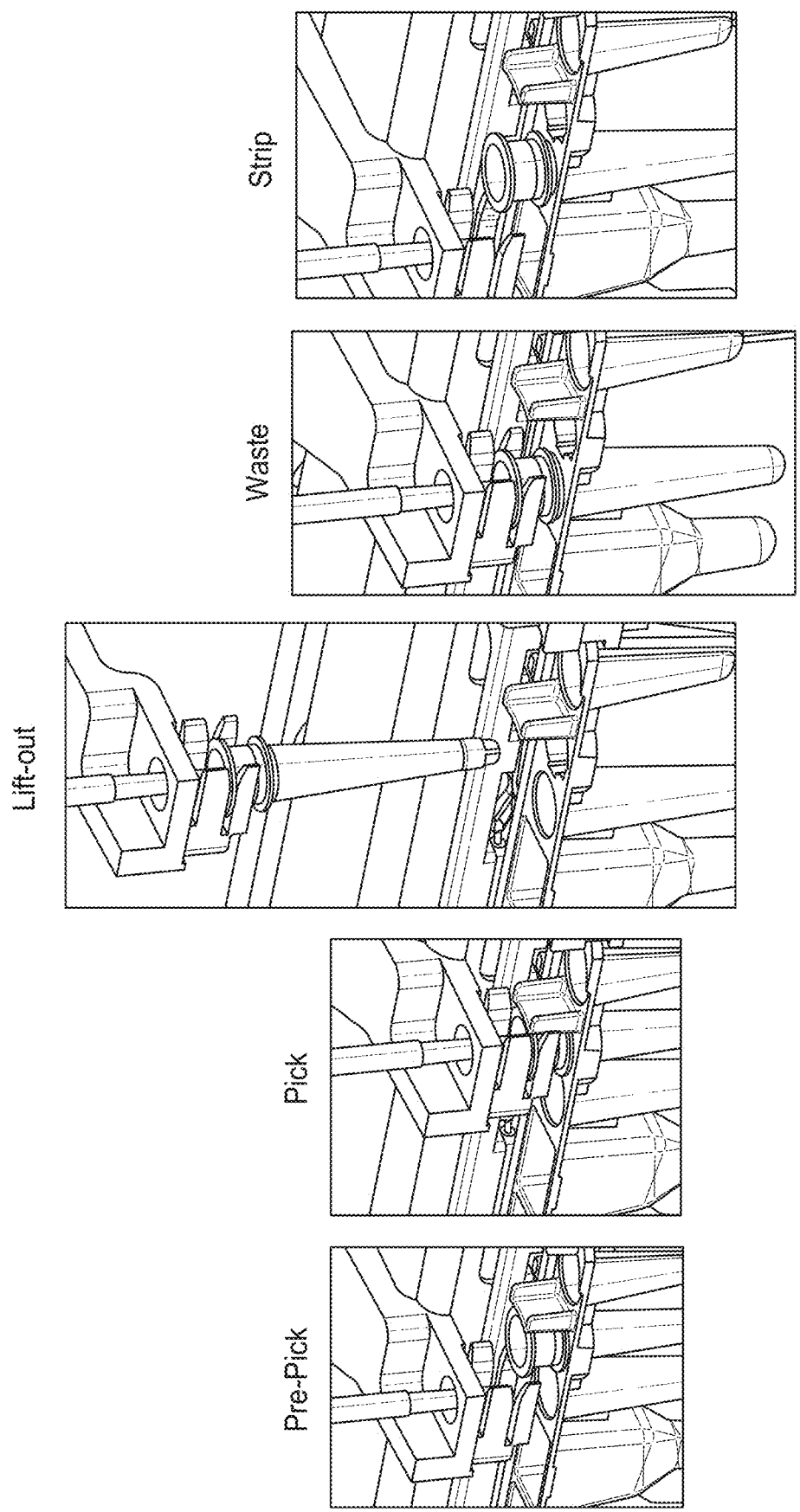
FIG. 12 shows the mechanical operations of the plunger holder element according to one embodiment of the disclosure.

In some embodiments, a plunger holder element or grasping component of a plunger bar comprises two arms that together form a slot that fits with specific grooves or one or more flanges on a plunger. One embodiment, a plurality of plungers (1100) connected to a plunger bar (1101) by plunger holder elements (1102) can be seen in FIG. 11. In addition, FIG. 12 shows one embodiment of a grasping component in various stages of connection with the plunger. The first panel (from the left; "Pre-Pick") shows how a grasping component moves in an axis perpendicular to the length of the plunger such that grooves found on the proximal end of a plunger slide into the slot of the grasping component (second panel; "Pick"). In some cases, the plunger arm may perform a movement prior to aligning with an element of the plunger to pick up the plunger, e.g., the plunger arm may perform a movement that repositions the plunger within the sample processing cartridge. In one embodiment, the plunger arm may perform a motion such that a portion of the plunger arm or an element attached thereto (e.g., the grasping component) is used to tap down the plunger, e.g., to seat the plunger in the sample processing cartridge. In some instances, seating the plunger in the sample processing cartridge assures that the gripper component properly aligns with the plunger during the "pre-pick" step. As depicted in FIG. 12, once the gripper component and the plunger are engaged, the plunger arm may vertically lift the plunger (middle panel; "lift-out") from the sample processing cartridge. Following use the plunger may be disengaged from the gripper component in any convenient manner, e.g., by positioning the plunger in a waste area (e.g., as depicted in FIG. 12, "Waste") and horizontally maneuvering the plunger arm (e.g., as depicted in FIG. 12, "Strip") to remove the plunger from the gripper component.

Any mechanism known in the art may be employed to secure the plunger within the grasping component. In some cases, a grasping component can be readily removed from a plunger arm, e.g., for routine cleaning or replacement. A grasping component may have a hole positioned such that a plunger magnet may be inserted through the hole and between the two arms.

In some embodiments, a plunger bar is attached to an actuator (e.g., linear actuator). In some cases, the plunger bar is attached to a pair of actuators (e.g., linear actuators), each of which is attached at each end of the length of the plunger bar. The pair of actuators may be configured to move the plunger magnet bar up and down an axis (e.g., z-axis, i.e., "vertically") at the same speed and direction such that the plurality of plungers attached via grasping components be simultaneously brought to proximity ('engaged' to), or away from ('dis-engaged' from) a processing well. For example, the plunger bar may be moved such that an attached plunger is inserted into a processing well. The pair of actuators allow for movement of the plunger magnet bar in an axis that is perpendicular to the length of the plunger magnet bar.

In some embodiments, a plunger bar is attached to an actuator that allows for movement in a horizontal plane. For example, a plunger bar will move in a horizontal plane so that a grasping component can engage a plunger. After a grasping component has engaged a plunger, movement in the z-axis brings the plunger up (e.g., up out of a processing well) or down (e.g., into a second processing well).

Figure 10:
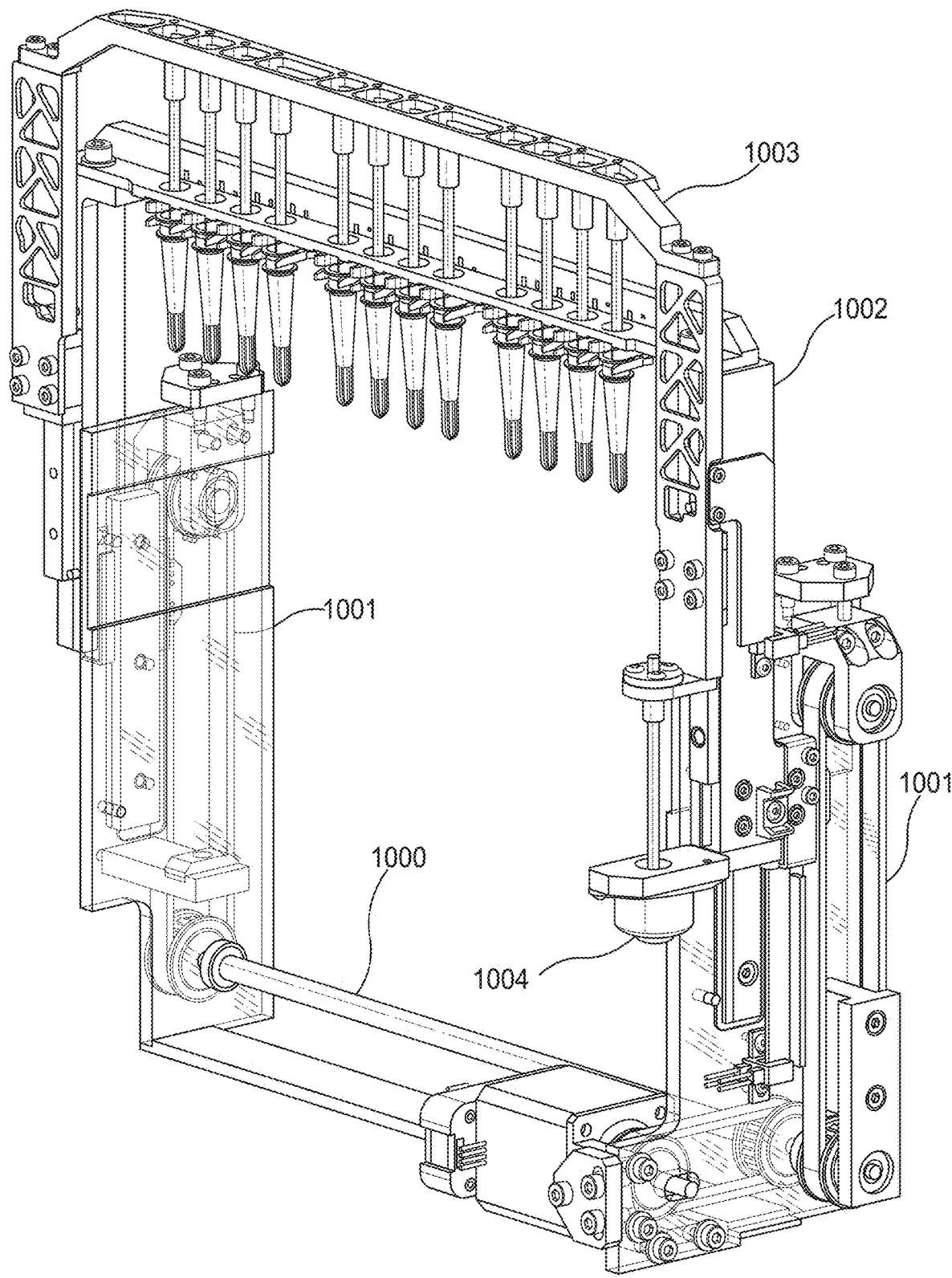
FIG. 10 shows three sets of four plungers affixed to a plunger bar and three sets of four magnets affixed to a magnet bar and other components according to one embodiment of the instant disclosure.

Any method known in the art may be used to power the movement of any actuators of the present disclosure. For example, a pulley and timing belt may be coupled to a belt tensioner that is driven by a z-axis stepper motor or encoder may be employed to power the movement of the actuators that allows a plunger magnet to engage and dis-engage a plunger. FIG. 10 shows one embodiment in which a drive shaft (1000) that is attached to drive pulleys (1001) on both sides of the drive shaft which are attached to a plunger bar's vertical arm (1002) which is attached to a magnet bar (1003).

In some embodiments, the plunger is used to mix a sample within a processing well. Mixing may be performed by a circular motion, a shaking motion, an up and down motion, or any motion known in the art to effectively mix a liquid sample. Aspects of this disclosure provide improved positioning of a plunger such that at the improved position, mixing by the plunger mixes the processing sample uniformly while minimizing the buildup of any contents of the processing well (e.g., magnetic microparticles) on the sides of the plunger and/or the sides of the well. In some cases, the plunger is positioned about 1 mm, about 1.5 mm, about 2 mm, about 2.5 mm, about 3 mm, about 3.5 mm, about 4 mm, about 4.5 mm, about 5 mm, about 5.5 mm about 6 mm, about 6.5 mm, about 7 mm, at least about 7 mm above the bottom of a processing well before mixing occurs. Mixing by a plunger at an improved position may prevent the formation of air pockets.

In some instances, a plunger bar may comprise fixed stopping points (e.g., hard stops) to prevent movement beyond a set range of motion. Hard stops may be strategically placed anywhere along the plunger bar such that the plunger bar cannot move past a certain range, to prevent any components of the plunger bar (e.g., grasping components) from, e.g., contacting any other component of a sample extraction and processing device, or from, e.g., crashing into a processing well. For example, a back hard stop may hit before the back ends of a plunger bar hits any other component of the device. In other cases, a front hard stop may hit before the front ends of any grasping components crash into a processing well.

In some embodiments, a plunger bar may comprise a home flag and home sensor. In some cases, a home flag may be attached to a plunger bar to allow for the zero-ing of the plunger bar when sensed by a home sensor. For example, a home sensor may be strategically placed on a device of the present disclosure that recognizes a home flag on a plunger bar. At any time during sample extraction and processing, a plunger bar may be zeroed using a home flag allowing the plunger bar to move the appropriate distance.

Plunger Magnet

An aspect of the present disclosure provides a magnetic field for use is a sample extraction and processing device of the present disclosure. For example, a plunger magnetic field provided by a plunger magnet may be used when employing a unique set of plunger and plunger magnet motions which ensure the proper processing of magnetic microparticles that a sample (e.g., nucleic acid sample) may be bound to. In one embodiment, the plunger magnetic field provided by the plunger magnet allows for the attraction of magnetic microparticles within a processing well (e.g., an elution well) to a plunger, and allows for, e.g., transfer of magnetic microparticles between processing wells, displacement of magnetic microparticles within a processing well for the proper mixing of the magnetic microparticles, etc.

A sample extraction and processing device of the present disclosure may include a plunger magnetic field that is positioned away from a processing well. In one embodiment, the plunger magnetic field is positioned sufficiently far away from a processing well such that the magnetic field has no effect on any magnetic microparticles that may be within the processing well. In another embodiment, the plunger magnetic field is positioned sufficiently far away from an elution well such that the magnetic field has no effect on any magnetic microparticles that may be within the elution well. In cases where the plunger magnetic field is positioned sufficiently far away from a processing well, the plunger magnetic field is considered to be in a 'dis-engaged' mode. By 'dis-engaged', as used herein, is meant any part (e.g., magnetic field) that is not in contact, or is sufficiently removed from a second part (e.g., processing well) such that the effects of any part are not experienced by the other.

In some embodiments, the source of a plunger magnetic field may fit within a plunger of the present disclosure. In such cases, the source of a plunger magnetic field may be configured to produce a magnetic field with a magnetic field strength that is capable of overcoming the plunger, such that magnetic microparticles may still be attracted to an ensheathed magnetic field. By "ensheathed", as used herein, is meant any part that is enclosed in a sheath. For example, a plunger magnet may be ensheathed by a plunger after insertion of the plunger magnet into the plunger.

The plunger magnetic field may be provided by a permanent magnet or an electromagnet or a plurality of ferromagnetic elements. In some cases, a plunger magnetic field may be provided by one or more electromagnets, such as coil electromagnets. The coil electromagnets may include wire-wound coils. The source of the plunger magnetic field may be configured to produce a magnetic field with a magnetic field strength, when the plunger magnetic field is in an 'engaged' mode, capable of attracting magnetic microparticles that may be present in a processing well. The strength of the external magnetic field may be configured such that when in an 'engaged' mode, magnetic microparticles that may be within a processing well will be attracted to a plunger. The source of the plunger magnetic field may be configured to produce a magnetic field with a magnetic field strength of 1 Oe or more, 5 Oe or more, 10 Oe or more, 20 Oe or more, 30 Oe or more, 40 Oe or more, 50 Oe or more, 60 Oe or more, 70 Oe or more, 80 Oe or more, 90 Oe or more, or 100 Oe or more.

In some cases, a plunger magnetic field source (e.g., a plunger magnet) is able to freely move along an axis (e.g., the z-axis). The movements of a plunger magnet may be constrained such that the plunger magnet does not physically interfere with other parts of a sample extraction and processing device of the present disclosure. The rotation of a plunger magnet may be constrained such that the magnetic field radiated by the plunger magnet does not interfere with other parts of a sample extraction and processing device of the present disclosure.

In one embodiment, a plunger magnet is able to freely move between two fixed points within the device, e.g., a point where the plunger magnet is 'dis-engaged' (e.g., positioned at a height above a processing well where magnetic microparticles within the processing well are not affected by the plunger magnetic field) and a point where the plunger magnet is 'engaged' (e.g., when the plunger magnet is inserted into a plunger positioned within a processing well). In some instances, the 'dis-engaged' point where a plunger magnet is positioned may be a 'home' position of the plunger magnet. As used herein, a 'home' position refers to the default position in which a moving part is found within a sample extraction and processing device of the present disclosure. As such, a plunger magnet moves from a home position (e.g., default position) to a second position in which it transitions into an 'engaged' mode. In some cases, the distance between two fixed points that the plunger magnet may freely move between, e.g., is about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, at least about 20 cm, at least about 25 cm, at least about 30 cm.

In some embodiments, the movement of a plunger magnet may include a third fixed point. A third fixed point may be a position that a plunger magnet moves to when a sample extraction and processing device is in 'standby' mode. By "standby", as used herein, is meant when a device is in a state of readiness, e.g., when the device is powered on, but is not actually functioning. A third "standby" fixed point may be useful for when general maintenance activities (e.g., cleaning, replacing parts, etc.) are required to be performed.

Figure 14:
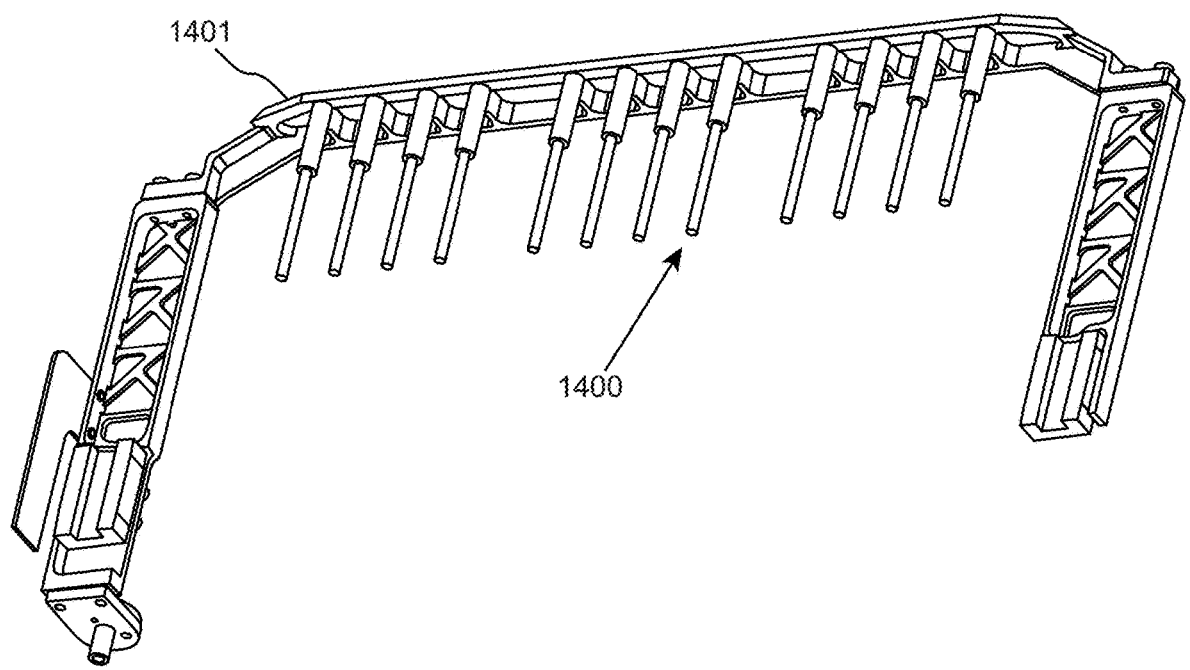
FIG. 14 shows a magnet bar that has four sets of three magnets affixed thereto according to one embodiment of the instant disclosure.

In order to achieve the desired movements of the plunger magnet, the system may include one or more actuators. By actuator is meant a device configured to move a part of a mechanism or system. Typically, actuators are operated by a source of energy, usually in the form of an electric current, hydraulic fluid pressure or pneumatic pressure, and convert that energy into a form of motion. Examples of actuators include, but are not limited to, a motor, a pneumatic actuator, a hydraulic piston, a piezoelectric actuator, a transducer, and the like. In some embodiments, the plunger magnet is affixed or adhered onto a plunger magnet bar which is attached to an actuator. For example, FIG. 14 shows the placement of a plunger magnet (1400) affixed to a plunger magnet bar (1401) and FIG. 10 shows such an arrangement where the plunger magnet bar (1003) that is connected to an actuator (1004) for vertical movement relative to the plunger bar (1002).

Figure 13C:
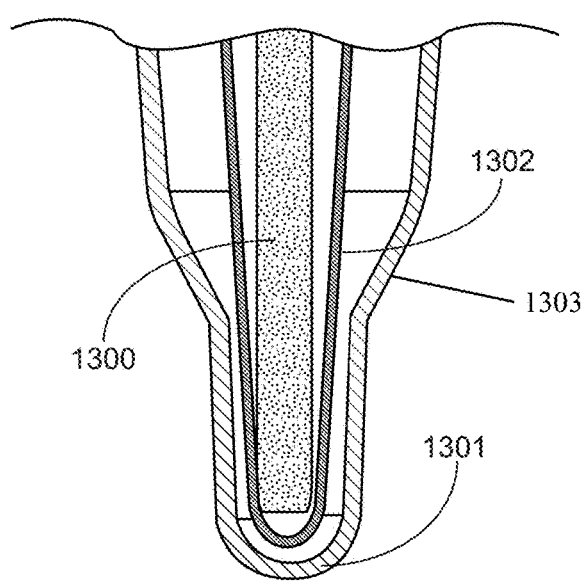

FIG. 13A-13B shows the movements of a plunger magnet between two vertical points. FIG. 13A shows one embodiment of the positioning of the plunger magnet (1300) in a 'dis-engaged' or 'up' mode, where the plunger magnet is positioned at a distance sufficiently far away from a processing well such that the magnetic field effects of the plunger magnet does not influence any magnetic microparticles that may be within the processing well. FIG. 13B shows one embodiment of the positioning of the plunger magnet (1300) in an 'engaged' or 'down' mode, where the plunger magnet is inserted into a plunger and the plunger with magnet is lowered to the bottom of a processing well (1301). In such an 'engaged' mode, any magnetic microparticles found within a processing well may be attracted to the plunger with magnet and magnetically 5 adhere to the plunger. FIG. 13C shows a zoomed in cut-away of the plunger with the magnet (1300) in the plunger (1302) at the bottom of the processing well (1301) and the magnet is in the 'engaged' mode within the plunger. FIG. 13C also shows the mid-well flare (1303) in the sample processing well that segments the sample processing well into a top volume and a bottom volume having different nominal diameters.

In some cases, the movement of a plunger magnet may be in concert with the movement of a plunger, e.g. the speed and direction in which the plunger magnet moves is the same as the speed and direction in which the plunger moves. In some cases, the movement of the plunger may drive the movement of the plunger magnet, e.g., when the plunger undergoes a shaking movement (e.g., a rapid continuous up and down motion) when mixing a sample within a processing well.

The home position of a plunger magnet may be a position that is sufficiently far away from a processing well such that the magnetic effects of the plunger magnet do not influence any materials (e.g., magnetic microparticles) found within the processing well. In some embodiments, the home position of the plunger magnet, e.g., is about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, at least about 20 cm, at least about 25 cm, at least about 30 cm away from a processing well.

In some instances, a plunger magnet in an 'engaged mode' (e.g., plunger magnet inserted into a plunger is positioned such that any materials within a processing well is influenced by the plunger with magnet) is used to attract magnetic microparticles onto a plunger. The plunger magnet is useful in attracting magnetic microparticles to a plunger for use during a mixing step of a sample extraction and processing protocol. The plunger magnet is useful in attracting magnetic microparticles to a plunger so that the magnetic microparticles can be transferred from one processing well to another processing well. For example, a plunger with plunger magnet when lowered into a processing well will attract magnetic microparticles to the plunger. Once all the magnetic microparticles are magnetically bound to the plunger, the plunger with plunger magnet may be removed from the first processing well and moved to a second processing well, where the plunger magnet is removed from the plunger and the magnetic microparticles are free to be in suspension within the second processing well. A person of skill in the art will recognize any combination of plunger magnet and plunger movements that will maximize the efficiency of moving magnetic microparticles within a sample extraction and processing protocol of the present disclosure.

Plunger Magnet Bar

Aspects of this disclosure provide a plunger magnet bar to which a plunger magnet is affixed to. The plunger magnet bar may be machined from any suitable materials that in general do not possess magnetic properties (i.e., materials that generally do not interfere with any magnetic fields). For example, a plunger magnet bar may be machined from a bar of aluminum. In some aspects, the plunger magnet bar will comprise a holder (or hole) at which the plunger magnet is affixed or adhered onto. In some cases, the plunger magnet bar will comprise more than one, more than two, more than three, more than four, more than five, more than six, more than seven, more than eight, more than ten, more than twelve, more than fourteen, more than sixteen, more than twenty holders, or holes, at which a plurality of plunger magnets is affixed or adhered onto. In one embodiment, three sets of four plunger magnets are adhered onto three sets of four holders, or holes, on a plunger magnet bar. In many cases, the positioning of the holders (or holes) along the plunger magnet bar is organized in such a way as to align the holders (and magnets that are affixed thereto) with the positioning of processing wells.

In some cases, a plunger magnet will be adhered on a plunger magnet bar with an assembly fixture to a precise position along the plunger magnet bar. In many cases, the precise position on a plunger magnet bar at which a plunger magnet is adhered onto is organized in such a way as to align the plunger magnet positions with the positioning of processing wells. In some instances, a plunger magnet is affixed or adhered onto a plunger magnet bar perpendicularly to the length of the plunger magnet bar (see, FIG. 14).

In some embodiments, a plunger magnet bar is attached to an actuator (e.g., linear actuator). In some cases, the plunger magnet bar is attached to a pair of actuators (e.g., linear actuators), each of which is attached at each end of the length of the plunger magnet bar. The pair of actuators may be configured to move the plunger magnet bar up and down an axis (e.g., z-axis) at the same speed and direction such that the plurality of plunger magnets affixed to a plunger magnet bar may be simultaneously brought to proximity ('engaged' to), or away from ('dis-engaged' from) a plunger. For example, the plunger magnet bar may be moved such that an affixed plunger magnet is inserted into or removed from a plunger. An actuator attached to the plunger bar can then control the movements of the plunger with plunger magnet inserted. In some cases, the movements of a plunger with plunger magnet inserted are controlled by an actuator attached to a plunger bar. The pair of actuators (e.g., linear actuators) allow for movement of the plunger magnet bar in an axis that is perpendicular to the length of the plunger magnet bar. Any method known in the art may be used to power the movement of any actuators of the present disclosure.

In some cases, a plunger magnet bar is moved such that a plunger magnet inserts into the bottom of a plunger quickly. For example, when a plunger is at the bottom of a processing well (e.g., an elution tube) that contains magnetic microparticles, quickly moving the plunger magnet to the bottom of the plunger ensures that magnetic microparticles are not attracted at the top of the processing well liquid (e.g., elution liquid) as the plunger magnet moves into position. In some cases, a plunger magnet bar is moved such that a plunger magnet is removed from a plunger quickly. Quick removal of the plunger magnet from the plunger ensures that magnetic microparticles do not follow the movement of the plunger magnet and remains near the bottom of the processing well.

In some instances, a plunger magnet bar may comprise fixed stopping points (e.g., hard stops) to prevent movement beyond a set range of motion. Hard stops may be strategically placed anywhere along the plunger magnet bar such that the plunger magnet bar cannot move past a certain range, to prevent any affixed plunger magnets from, e.g., contacting any other component of a sample extraction and processing device, or from, e.g., crashing into a plunger. For example, a back hard stop may hit before the back ends of a plunger magnet bar hits any other component of the device. In other cases, a front hard stop may hit before the front ends of any plunger magnets crash into a plunger or processing well.

In some embodiments, a plunger magnet bar may comprise a home flag and home sensor. In some cases, a home flag may be attached to a plunger magnet bar to allow for the zero-ing of the plunger magnet bar when sensed by a home sensor. For example, a home sensor may be strategically placed on a device of the present disclosure that recognizes a home flag on a plunger magnet bar. At any time during sample extraction and processing, a plunger magnet bar may be zeroed using a home flag allowing the plunger magnet bar to move the appropriate distance.

External Magnet

Devices and methods utilizing devices as described herein may or may not make use of an external magnet in the sample processing as described herein. Thus, in some instances, a device of the instant disclosure will not include an external magnet as described herein. In other instances, a device of the instant disclosure will include an external magnet as described herein.

External magnetic fields may find use in retaining magnetic particles within a processing well. A sample extraction and processing device of the present disclosure may include an external magnetic field positioned away from a processing well. In one embodiment, the external magnetic field is positioned sufficiently far away from a processing well such that the magnetic field has no effect on any magnetic microparticles that may be within the processing well. In another embodiment, the external magnetic field is positioned sufficiently far away from an elution well such that the magnetic field has no effect on any magnetic microparticles that may be within the elution well. In cases where the external magnetic field is positioned sufficiently far away from a processing well, the external magnetic field is considered to be in a 'dis-engaged' mode. By 'dis-engaged', as used herein, is meant any part (e.g., magnetic field) that is not in contact, or is sufficiently removed from a second part (e.g., processing well) such that the effects of any part are not experienced by the other.

The external magnetic field may be provided by a permanent magnet or an electromagnet or a plurality of ferromagnetic elements. In some cases, an external magnetic field may be provided by one or more electromagnets, such as coil electromagnets. The coil electromagnets may include wire-wound coils. The source of the external magnetic field may be configured to produce a magnetic field with a magnetic field strength, when the external magnetic field is in an 'engaged' mode, capable of attracting magnetic microparticles that may be present in a processing well. The strength of the external magnetic field may be configured such that when in an 'engaged' mode, magnetic microparticles that may be within a processing well retain in the processing well. The source of the external magnetic field may be configured to produce a magnetic field with a magnetic field strength of 1 Oe or more, 5 Oe or more, 10 Oe or more, 20 Oe or more, 30 Oe or more, 40 Oe or more, 50 Oe or more, 60 Oe or more, 70 Oe or more, 80 Oe or more, 90 Oe or more, or 100 Oe or more.

In some cases, an external magnetic field source (e.g., an external magnet) is able to freely rotate about an axis. The rotation of an external magnet may be constrained such that the external magnet does not physically interfere with other parts of a sample extraction and processing device of the present disclosure. The rotation of an external magnet may be constrained such that the magnetic field radiated by the external magnet does not interfere with other parts of a sample extraction and processing device of the present disclosure. In one embodiment, an external magnet is able to freely rotate between two fixed points within the device, e.g., a point where the external magnet is 'dis-engaged' and a point where the external magnet is 'engaged'. In some instances, the 'dis-engaged' point where an external magnet is positioned may be a 'home' position of the external magnet. As used herein, a 'home' position refers to the default position in which a moving part is found within a sample extraction and processing device of the present disclosure. As such, an external magnet rotates from a home position (e.g., default position) to a second position in which it transitions into an 'engaged' mode. In some cases, the external magnet may rotate about 120° between two fixed points, e.g. about 100°, about 105°, about 110°, about 115°, about 125°, about 130°, about 135°, about 140°, at least about 140° between two fixed points.

In order to achieve the desired movements of the external magnet, the system may include one or more actuators. By actuator is meant a device configured to move a part of a mechanism or system. Typically, actuators are operated by a source of energy, usually in the form of an electric current, hydraulic fluid pressure or pneumatic pressure, and convert that energy into a form of motion. Examples of actuators include, but are not limited to, a motor, a pneumatic actuator, a hydraulic piston, a piezoelectric actuator, a transducer, and the like. In some embodiments, the external magnet is affixed or adhered onto an external magnet bar which is attached to an actuator. For example, the placement of an external magnet affixed to an external magnet bar that is connected to a rotating actuator. In one embodiment the positioning of the external magnet may be moved from a 'dis-engaged' mode to an 'engaged' mode, where in the dis-engaged' mode the magnet is positioned at a distance sufficiently far away from a processing well such that the magnetic field effects of the external magnet does not influence any magnetic microparticles that may be within the processing well. In the 'engaged mode' the positioning of the center of the external magnet center nominally is in contact with the processing well, e.g., at the cone transition of the processing well.

The home position of an external magnet may be a position that is sufficiently far away from a processing well such that the magnetic effects of the external magnet do not influence any materials (e.g., magnetic microparticles) found within the processing well. In some embodiments, the home position of the external magnet is about 26 mm away from a processing well, e.g. 26 mm away from the cone transition of the processing well, i.e., the distance between the center of the external magnet when in the home position is about 26 mm away from the cone transition of a processing well, e.g. about. In some cases, the distance between the center of the external magnet in a home position and a processing well is about 8 mm, about 9 mm, about 10 mm, about 12 mm, about 14 mm, about 16 mm, about 18 mm, about 20 mm, about 22 mm, about 24 mm, about 26 mm, about 28 mm, about 30 mm, about 32 mm or more.

In some instances, an external magnet in an 'engaged mode' (e.g., external magnet's center nominally is in contact with a processing well, e.g., at the cone transition of the well) is used to retain any magnetic microparticles within a processing well. The external magnet is particularly useful in retaining magnetic microparticles within an elution well to improve the consistency and efficiency of an elution process during sample extraction. In some cases, the movements of the external magnet relative to an elution well are in concert with the above-described motions of a plunger during the elution process. For example, prior to each mixing step of an elution process, when a plunger magnet is moved quickly above the elution tube to prevent magnetic particles from being attracted to it, engaging an external magnet with the elution well may improve the elution process by attracting magnetic particles within the elution well to the bottom, minimizing the amount of magnetic particles attracted to the surface of the elution well and sides of the plunger as the plunger magnet is repositioned. A person of skill in the art will recognize any combination of external magnet movements and plunger motions that will maximize the retaining of magnetic microparticles within a processing well.

In some instances, devices not having an external magnet will employ movement methods, as described herein, to prevent particular undesirable results associated with the movement of magnetic particles away from the bottom of the processing well.

External Magnet Bar

Devices and methods utilizing devices as described herein may or may not make use of an external magnet, and thus may or may not make use of an external magnet bar, in the sample processing as described herein. Thus, in some instances, a device of the instant disclosure will not include an external magnet bar as described herein. In other instances, a device of the instant disclosure will include an external magnet bar as described herein.

Aspects of this disclosure provide an external magnet bar to which an external magnet is affixed to. The external magnet bar may be machined from any suitable materials that in general do not possess magnetic properties (i.e., materials that generally do not interfere with any magnetic fields). For example, an external magnet bar may be machined from a bar of aluminum. In some aspects, the external magnet bar will comprise a holder (or hole) at which the external magnet is affixed or adhered onto. In some cases, the external magnet bar will comprise more than one, more than two, more than three, more than four, more than five, more than six, more than seven, more than eight, more than ten, more than twelve, more than fourteen, more than sixteen, more than twenty holders, or holes, at which a plurality of external magnets is affixed or adhered onto. In one embodiment, three sets of four external magnets are adhered onto three sets of four holders, or holes, on an external magnet bar. In many cases, the positioning of the holders (or holes) along the external magnet bar is organized in such a way as to align the holders (and magnets that are affixed thereto) with the positioning of processing wells.

In some cases, an external magnet will be adhered into an external magnet bar with an assembly fixture to a precise position along the external magnet bar. In many cases, the precise positions on an external magnet bar at which an external magnet is adhered onto is organized in such a way as to align the external magnet positions with the positioning of processing wells.

In some instances, an external magnet is affixed or adhered onto an external magnet bar at an angle, such that when the external magnet is 'engaged', the center of the external magnet nominally contacts the cone transition of an elution well. In one embodiment, the surface of the external magnet that is nominally in contact with the cone transition of an elution well is at a tangent to the cone transition angle of the elution well. In some cases, the surface of the center of the external magnet forms equal angles with either face flanking the cone transition angle of the elution well. The external magnet that is affixed or adhered onto an external magnet bar is done so at an angle, such that when the external magnet is 'dis-engaged', the external magnet is positioned so that it does not interfere with the rest of the sample extraction device. In some cases, when the external magnet is 'dis-engaged', the center of the external magnet faces in a direction that is perpendicular to the length of the external magnet bar.

In some embodiments, an external magnet bar is attached to an actuator. In some cases, the external magnet bar is attached to a pair of rotating actuators, each of which is attached at each end of the length of the external magnet bar.

The pair of rotating actuators may be configured to rotate at the same speed and direction such that the plurality of external magnets affixed to an external magnet bar may be brought to proximity ('engaged' to), or away from ('disengaged' from) a processing well (e.g., an elution well) simultaneously. The pair of rotating actuators rotates about an axis that is parallel to the length of an external magnet bar. Any method known in the art may be used to power the rotation of any actuators of the present disclosure. For example, a pulley and timing belt may be coupled to a belt tensioner that is driven by a stepper motor may be employed to power the rotation of the actuators that allow external magnets to engage and dis-engage a processing well.

In some instances, an external magnet bar may comprise fixed stopping points (e.g., hard stops) to prevent movement beyond a set range of motion. Hard stops may be strategically placed along the external magnet bar such that the external magnet bar cannot move past a certain range, to prevent any affixed external magnets from contacting any other component of the device. For example, a back hard stop may hit before the back ends of any external magnets hit any other component of the device. In other cases, a front hard stop may hit before the front ends of any external magnets hit any other component of the device.

In some embodiments, an external magnet bar may comprise a home flag and home sensor. In some cases, a home flag may be attached to an external magnet bar to allow for the zero-ing of the external magnet bar when sensed by a home sensor. For example, a home sensor may be strategically placed on a device of the present disclosure that recognizes a home flag on an external magnet bar. At any time during sample extraction and processing, an external magnet bar may be zeroed using a home flag allowing the external magnet bar to move the appropriate distance.

Control Circuitry

Devices and methods of the instant disclosure include automated electrically controlled components the operation of which may be controlled by one or more control circuits. In some instances, control circuits of the instant disclosure may include hardware control components. In some instances, control circuits of the instant disclosure may include software control components. As such, in some instances, devices of the instant disclosure may include programming e.g., stored on one or more computer memories and/or computer readable mediums for carrying out a method or process as described herein by one or more devices or device components as described herein. Programming of the instant disclosure may, in some instances, be written on non-transitory computer memory and/or on non-transitory computer readable medium.

Electrically controlled components of the described systems may be attached to each other and/or to control circuitry by any convenient means of electrical communication including wired and wireless means.

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

The devices and systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer harddrive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., actuatable components, power sources, etc.

As described above, devices of the instant disclosure may include one or more computer readable mediums, including non-transitory computer readable medium, which stores instructions for methods described herein. Aspects of the instant disclosure include computer readable medium storing instructions that, when executed by a computing device, cause the computing device to perform one or more steps of a method as described herein.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as any many others.

The following examples are offered by way of illustration and not by way of limitation.

Examples

Example 1: Improved Consistency of Elution During Sample Extraction

Figure 4:
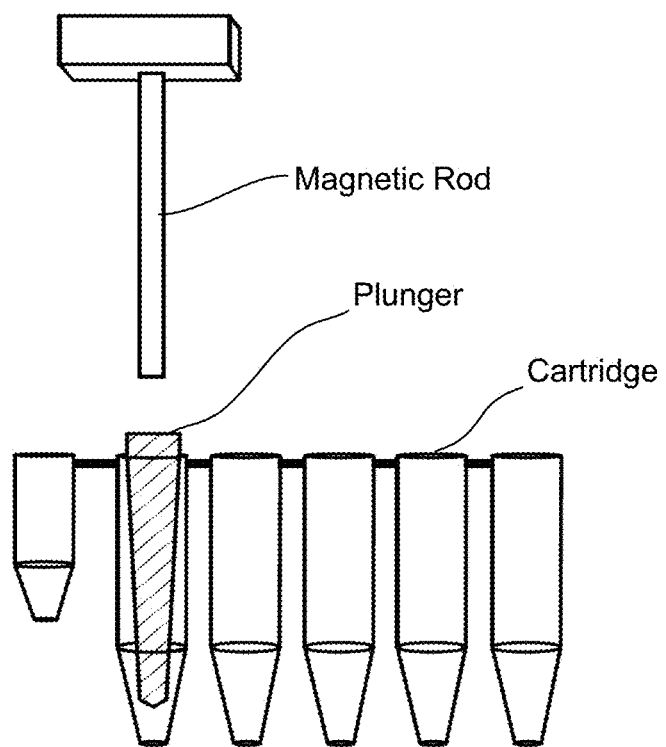
FIG. 4 shows a schematic of a magnet inserted into a plunger used in an automated sample extraction device according to one embodiment of the present disclosure.

The sample extraction process employs a series of automated steps involving a movable plunger and plunger magnet. To recover the nucleic acids, the plunger is used to mix the sample in the presence of magnetic particles. The plunger magnet is then inserted into the plunger and attracts the magnetic microparticles to which the sample nucleic acids are bound (FIG. 4). The plunger (with plunger magnet inside) and particles are then moved to the next processing well. The plunger magnet is retracted, the particles are released, and the process is repeated until the lysis, wash, and elution steps are completed (FIG. 5).

FIG. 4 depicts a schematic of a movable plunger and plunger magnet. The plunger is inserted into the processing well of the cartridge. The magnetic rod is inserted into the plunger to attract magnetic microparticles within the well during a typical process flow. Following early processes the plunger with magnetic rod inserted may be used to transfer the nucleic acid attached magnetic particles to an elution tube.

Figure 5A:
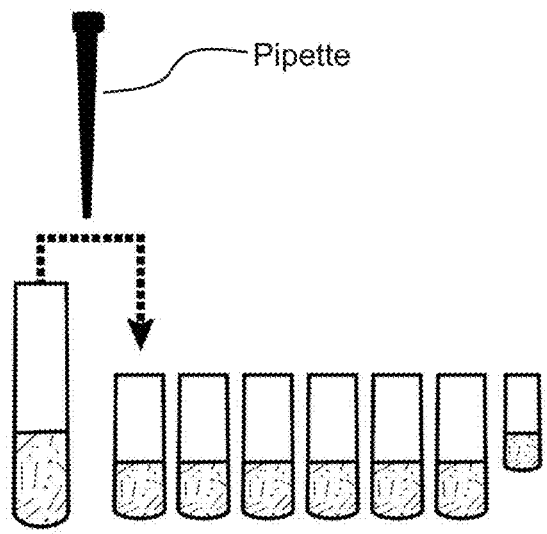
FIGS. 5A-5D depict the process flow that an automated sample extraction device follows according to one embodiment of the instant disclosure.
Figure 5B:
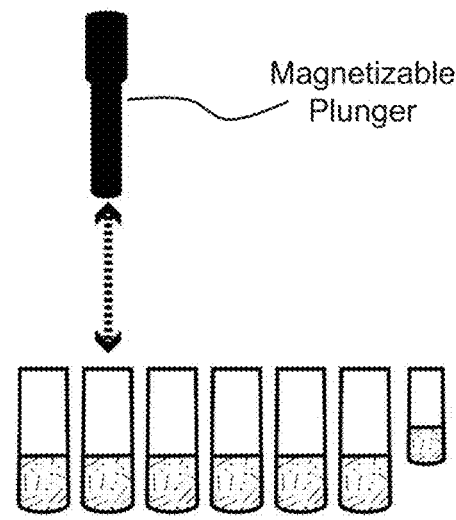
Figure 5C:
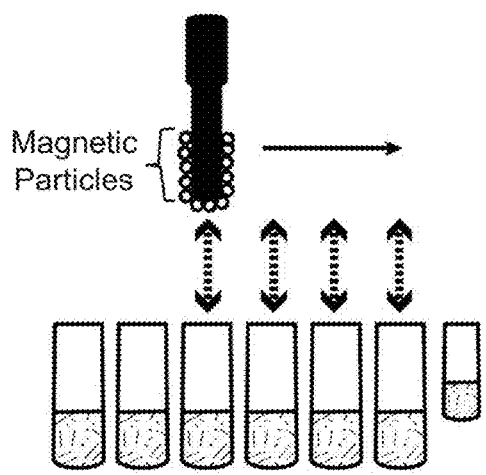
Figure 5D:
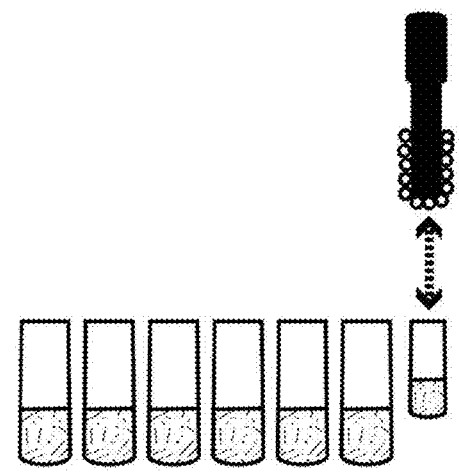

FIG. 5A-D depicts a typical process flow involving a series of automated steps in which the movable plunger and plunger magnet is used to transfer magnetic microparticles between different wells. FIG. 5A depicts the sample setup step of the process flow: on the left, depicts the addition of sample with pre-lysis, and on the right, depicts the addition of sample without pre-lysis. FIG. 5B depicts the lysis step of the process flow: on the left, the plunger without the plunger magnet provides constant mixing of the lysis well contents. On the right, the plunger magnet is inserted into the plunger and allows for the transfer of magnetic microparticles into the next well. FIG. 5C depicts the washing step of the process flow, wherein repeats of insertion and removal of the plunger magnet into the plunger allows for consecutive transfers and washings of the magnetic microparticles in consecutive wells. FIG. 5D depicts the elution step of the process flow wherein the magnetic microparticles are removed, and the eluate is transferred to the next module of an automated analysis system.

In order to obtain consistent results, all the magnetic microparticles must be transferred between wells and subsequently released from the plunger and uniformly mixed. This is particularly difficult in the elution well due to the tight fit of the plunger within the elution tube and low elution liquid volumes utilized.

FIG. 6 depicts a schematic representation of one example showing the tight fit of the plunger within the elution tube. Small elution liquid volumes are displaced into the space between the plunger and walls of the tube.

Figure 7A:
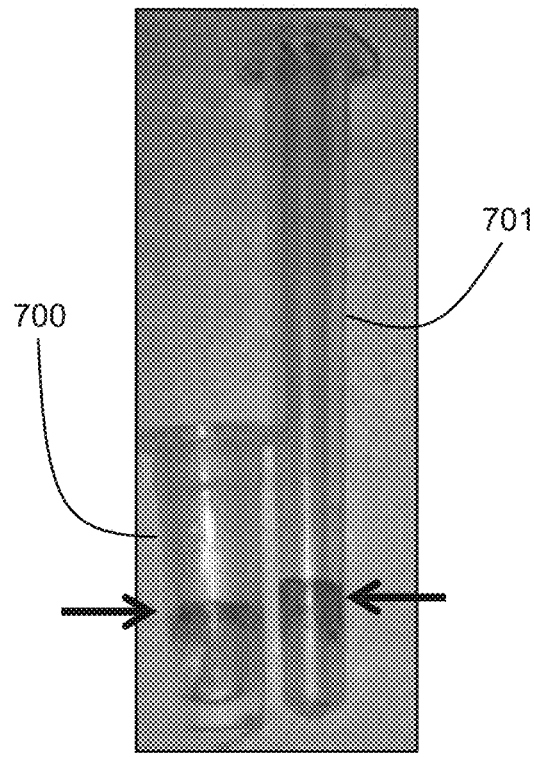
FIGS. 7A-7B depicts the amount of magnetic microparticles that adhere to the plungers used according to different methods as described herein.
Figure 7B:
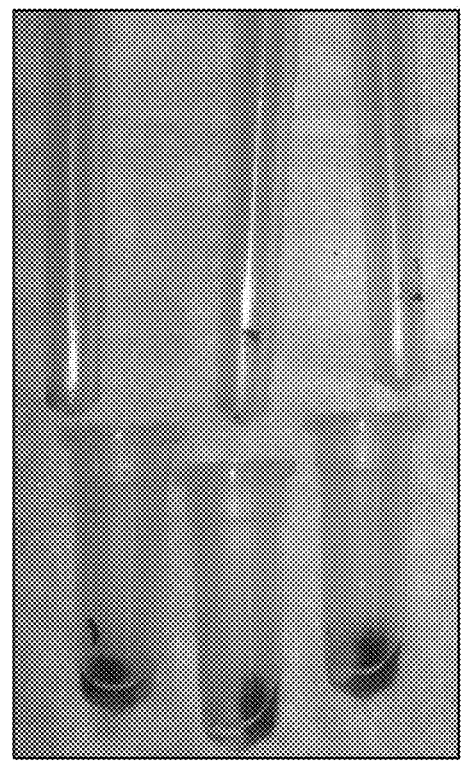

Problems which arise during the elution process include the formation of air pockets, inadequate release of the particles into the elution liquid, and buildup of the particles on the plunger and elution tube during the elution process. For example, FIG. 7A demonstrates the accumulation of particles (arrows) on the sides of the processing tube (700) and the plunger (701) as results from a conventional process not utilizing the methods as described herein. Each of the described issues causes inconsistency in how the nucleic acids elute from the particles and may ultimately affect the real-time PCR (RT-PCR) results. FIG. 7B depicts fewer magnetic microparticles adhered to the plunger and sides of the processing tube when methods of the instant disclosure are employed as described herein.

The issues described can be significantly reduced by employing a unique set of plunger and plunger magnet motions. These motions allow for consistent release of the particles from the plunger and adequate mixing of the particles while minimizing sticking to the elution tube and plunger (see, TABLE 1). In a particular embodiment, the described process begins after the particles are transferred from the last wash step into the elution well.

TABLE 1

Plunger and plunger magnet motions

| Step | Motion | Comment |
| --- | --- | --- |
| 1 | Move plunger/magnet into eluate well | Plunger magnet is inside plunger and particles are attached to plunger. Proper location of the magnet minimizes carryover of contaminants. |
| 2 | Move plunger/magnet to bottom of elution tube | Plunger magnet holds the plunger straight. Plunger is forced against elution tube bottom. Their "v" shapes cause the plunger to center in the elution tube. This forces any air pockets out and causes the liquid to rise uniformly around all sides of the plunger. |
| 3 | Retract plunger magnet out of plunger | Particles are now free from magnetic field and able to release into the elution liquid. |
| 4 | Mix slowly for 10 cycles at bottom of elution tube | Particles are washed off all sides of the plunger and air pockets are forced out. |
| 5 | Move plunger to bottom of elution tube | This is the starting point for mixing. At this point all the particles are released or submerged in the liquid. |
| 6 | Move plunger magnet to plunger bottom quickly | Particles are attracted to the bases of the plunger which is at the bottom of the elution tube. It is moved quickly to ensure particles are not attracted at the top of the liquid as it moves into position. |
| 7 | Pause 4 seconds | Pause to allow particles to move to magnet. It takes ~seconds for the particles to be pulled in. This keeps the particles |

TABLE 1-continued

Plunger and plunger magnet motions

| Step | Motion | Comment |
|---|---|---|
| 8 | Move plunger magnet quickly above elution tube | away from the surface of the liquid and thus prevents it from sticking to the plunger and elution tube. Retracting the plunger magnet allow particles to be free in the elution liquid. It is moved quickly and stops far enough away to prevent the particles from following it or being attracted to it as the next step proceeds. |
| 9 | Mix | Mix by moving the plunger at a speed and duration to give good mixing but minimize the particle collection at the surface. |
| 10 | Move plunger to bottom of elution tube | Moving the plunger to bottom of tube pushes the liquid to its maximum height ensuring the upper portions of the plunger and elution tube are "rinsed". This is also the position needed for the next magnet movement. |
| 11 | Repeat steps 6-10 for 10 minutes | This sequence will allow a 10 minute elution process while minimizing the buildup of particles on the plunger and elution tube. |
| 12 | Move plunger to above elution tube very slowly | Moving the plunger very slowly will reduce the amount of liquid that sticks to the plunger. |

Following step 12 the eluate is ready for removal or further processing

The unique set of plunger and plunger magnet motions ensures that the magnetic microparticles are released into the elution fluid and mixed uniformly while minimizing the particle build-up without adding any time to the process. As a result, the process of eluting the nucleic acids from the particles is more consistent from sample to sample. The amount of microparticles that remain on the plunger is dramatically reduced. Statistically significant improvement in elution efficiency and reduction in variability is observed between the conventional and herein described methods.

Figure 8:
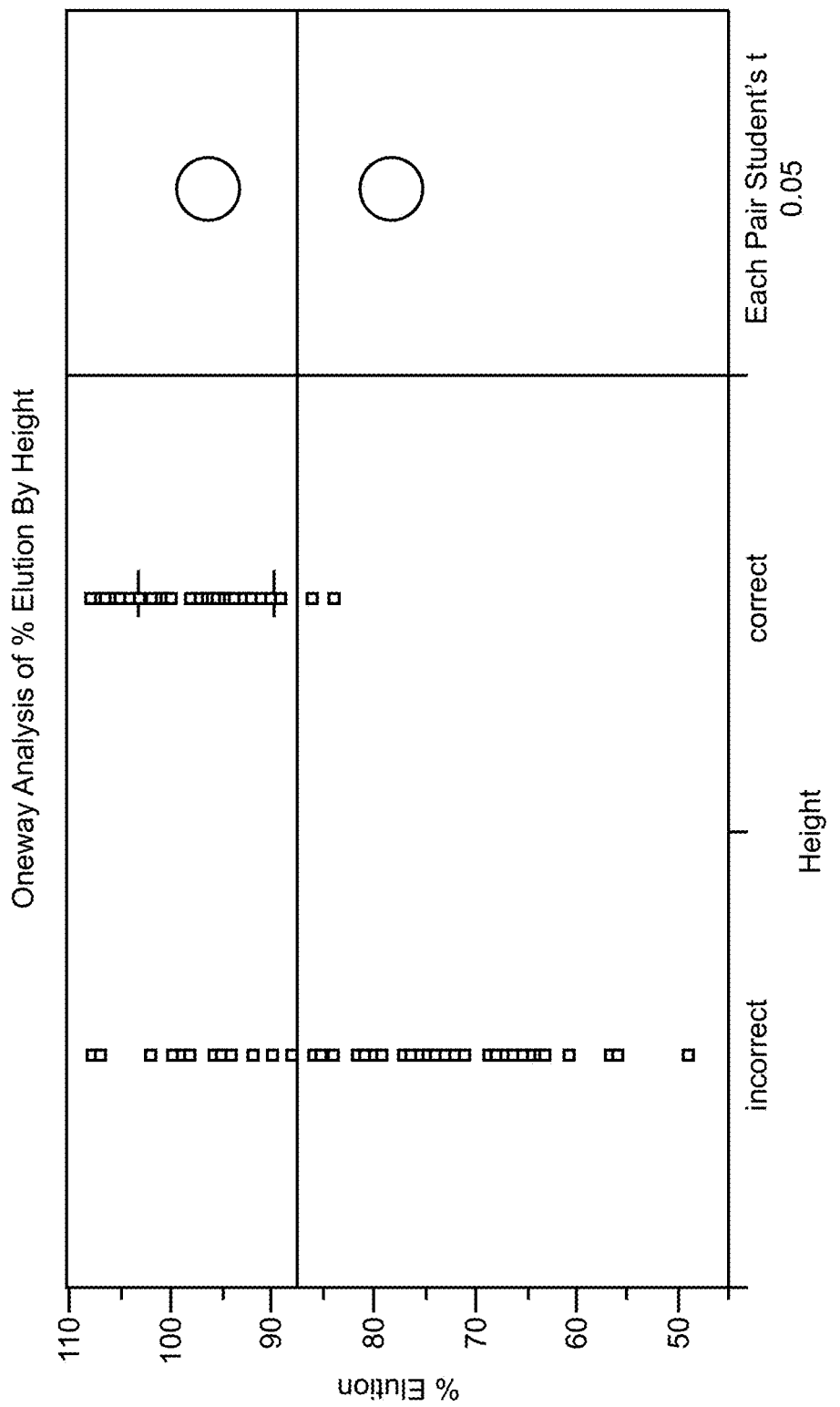
FIG. 8 shows a graphic representation of the percentage of microparticles eluted according to various elution positions of a plunger.

For example, FIG. 8 provides an example of how carefully controlling sample processing parameters positively impacts elution efficiency and reduces variability. Specifically, FIG. 8 graphically depicts an analysis of percentage elution by plunger position height. As shown, when the height of the plunger was at an incorrect level ("incorrect"), the mean percentage elution was 78.5714±1.9238 (reporting the standard error of the mean). However, when the height of the plunger was at a correct level, the mean percentage elution was 96.5397±0.8363 (reporting the standard error of the mean) and much less variability was seen in the resulting elution. Thus, careful control of the elution motion parameters measurably affects elution outcome.

Notwithstanding the appended claims, the disclosure is also defined by the following clauses:

1. A plunger for sample processing in an automated sample processing device, the plunger comprising an elongated hollow cone structure comprising:
an open top;
a closed rounded tip comprising an end nub; and
a plurality of flutes arranged parallel to the long axis of the elongated hollow cone structure that extend from the closed rounded tip less than the entire length of the elongated hollow cone structure.

2. The plunger according to clause 1, wherein the plurality of flutes extend from the closed rounded tip less than half the entire length of the elongated hollow cone structure.

3. The plunger according to any one of clauses 1-2, wherein the elongated hollow cone structure is configured to receive a plunger magnet inserted through the open top.

4. The plunger according to clause 3, wherein the plunger magnet has a maximum diameter essentially equal to the minimum diameter inside the hollow cone structure.

5. The plunger according to any one of clauses 1-4, wherein the elongated hollow cone structure comprises a wall with a nominal thickness between 0.15 mm to 0.45 mm.

6. The plunger according to any one of clauses 1-5, wherein the elongated hollow cone structure comprises a maximum diameter adjacent to the closed rounded tip equal to the smallest diameter of a sample processing well.

7. The plunger according to any one of clauses 1-6, wherein the volume of space ascribed to the flutes, as determined from the difference in volume between the plunger and an identical plunger without the plurality of flutes, is between 10 $mm^3$ and 100 $mm^3$.

8. The plunger according to any one of clauses 1-7, wherein the plurality of flutes comprises three or more flutes.

9. The plunger according to clause 8, wherein the plurality of flutes comprises four or more flutes.

10. The plunger according to clause 9, wherein the plurality of flutes comprises five or more flutes.

11. The plunger according to clause 10, wherein the plurality of flutes is six flutes.

12. The plunger according to any one of clauses 1-11, wherein the elongated hollow cone structure comprises two or more different tapers.

13. The plunger according to clause 12, wherein the two or more different tapers comprise a first taper adjacent to the fluted region and a second taper adjacent to the open top.

14. The plunger according to clause 13, wherein the first taper is greater than the second taper.

15. The plunger according to any one of clauses 1-14, wherein the plunger further comprises a plunger holder element configured to allow coupling of the plunger to a plunger manipulator.

16. The plunger according to clause 15, wherein the plunger holder element is a flange encircling the open top.

17. The plunger according to any one of clauses 1-16, wherein the elongated hollow cone structure further comprises a stacking spacer.

The plunger according to clause 17, wherein the stacking spacer comprises a flange encircling the circumference of the hollow cone structure.

19. The plunger according to clause 17, wherein the stacking spacer comprises a plurality of aligned ribs arranged parallel with the long axis of the elongated hollow tube.

20. A system for sample processing in an automated sample processing device, the system comprising:
a sample processing well; and
a plunger comprising an elongated hollow cone structure comprising:
an open top;
a closed rounded tip comprising an end nub;

a diameter adjacent to the closed rounded tip equal to the smallest diameter of the sample processing well; and a plurality of flutes arranged parallel to the long axis of the elongated hollow cone structure extending from the closed rounded tip, wherein the sample processing well is configured to receive and align the plunger to the center of the sample processing well when the plunger is inserted into the sample processing well.

21. The system according to clause 20, wherein the sample processing well comprises a cone shaped bottom.

22. The system according to clause 20, wherein the sample processing well comprises a dome shaped bottom.

23. The system according to any one of clauses 20-22, wherein the plunger and the sample processing well are configured such that, upon complete insertion of the plunger into the sample processing well, the nub contacts the bottom of the sample processing well.

24. The system according to any one of clauses 20-23, wherein the plurality of flutes extend from the closed rounded tip less than the entire length of the elongated hollow cone structure.

25. The system according to clause 24, wherein the plurality of flutes extend from the closed rounded tip less than half the entire length of the elongated hollow cone structure.

26. The system according to any one of clauses 20-25, wherein the sample processing well comprises a mid-well flare in the sample processing well diameter that segments the sample processing well into a top volume and a bottom volume having different nominal diameters.

27. The system according to clause 26, wherein the nominal diameter of the bottom volume is essentially equal to the maximum diameter of the fluted portion of the plunger.

28. The system according to any one of clauses 26-27, wherein the nominal diameter of the top volume is greater than the maximum diameter of the fluted portion of the plunger.

29. The system according to clause 28, wherein the nominal diameter of the top volume is at least 1.1 times greater than the maximum diameter of the fluted portion of the plunger.

30. The system according to any one of clauses 26-29, wherein when the plunger is inserted completely into the sample processing well the plurality of flutes do not extend to the level of the top volume.

31. The system according to clause 30, wherein when the plunger is inserted completely into the sample processing well the plurality of flutes extend from the closed rounded tip essentially to the level of the mid-well flare.

32. The system according to any one of clauses 26-31, wherein the mid-well flare comprises 50% or less of the length of the sample processing well.

33. The system according to any one of clauses 26-32, wherein the sample processing well and the plunger are configured such that upon insertion of the plunger into the sample processing well sample processing buffer does not rise above the mid-well flare.

34. The system according to any one of clauses 20-33, wherein the sample processing well is an elution well and upon complete insertion of the plunger into the elution well the empty volume enclosed by the elution well and the plurality of flutes does not exceed the elution well buffer volume.

35. The system according to clause 34, wherein the elution well buffer volume is between 10 µl and 100 µl.

36. The system according to any one of clauses 20-35, wherein the sample processing well is contained in a sample processing cartridge.

37. The system according to clause 36, wherein the system comprises a plurality of plungers and the sample processing cartridge comprises a plurality of sample processing wells equal to the number of plungers.

38. The system according to clause 37, wherein the number of plungers and number of sample processing wells are three or more.

39. The system according to any one of clauses 36-38, wherein the system comprises a plurality of sample processing cartridges each comprising a plurality of sample processing wells and a plurality of plungers equal to the total number of sample processing wells of the system.

40. The system according to any one of clauses 20-39, wherein the system further comprises a plunger manipulator configured to physically manipulate the plunger in at least a vertical direction.

41. The system according to clause 40, wherein the plunger manipulator comprises a plunger grasping mechanism.

42. The system according to any one of clauses 40-41, wherein the plunger manipulator is a plunger bar.

43. The system according to clause 42, wherein the plunger bar comprises a plurality of plunger grasping mechanisms corresponding to the number of plungers of the system.

44. The system according to any one of clauses 20-43, wherein the system further comprises a plunger magnet configured to be inserted through the open top of the plunger.

45. The system according to clause 44, wherein the system further comprises a plunger magnet manipulator attached to the plunger magnet and configured to physically manipulate the plunger magnet in at least a vertical direction.

46. The system according to clause 45, wherein the plunger magnet manipulator is a plunger magnet bar comprising a plurality of plunger magnets equal to the number of plungers of the system.

47. The system according to any one of clauses 40-43, wherein the plunger manipulator is further configured to be translated in at least one horizontal direction.

48. The system according to any one of clauses 45-47, wherein the plunger magnet manipulator is further configured to be translated in at least one horizontal direction.

49. The system according to clause 48, wherein the sample processing cartridge comprises at least one additional processing well adjacent to each sample processing well and the horizontal translation of the plunger manipulator is configured to allow movement of each plunger from an additional processing well to a sample processing well.

50. The system according to clause 49, wherein the horizontal translation of the plunger magnet manipulator is coincident with the horizontal translation of the plunger manipulator.

51. The system according to clause 50, wherein the plunger manipulator and the plunger magnet manipulator are physically linked.

52. A method of eluting nucleic acid from attached magnetic particles, the method comprising:
   a) inserting into an elution well comprising an elution buffer a magnetized plunger comprising magnetically attached magnetic particles comprising attached nucleic acid;

b) driving the magnetized plunger to the bottom of the elution well to center the magnetized plunger in the elution well;
c) retracting a magnet out of the plunger to demagnetize the plunger;
d) reciprocating the demagnetized plunger up and down in the elution buffer at a first vertical speed sufficient to elute the nucleic acid; and
e) removing the plunger from the elution buffer at a second vertical speed, wherein the second vertical speed is slower than the first vertical speed.

53. The method according to clause 52, wherein the method further comprises two or more steps of driving the demagnetized plunger to the bottom of the elution well to center the demagnetized plunger in the elution well.

54. The method according to any one of clauses 52-53, wherein the driving the demagnetized plunger to the bottom of the elution well to center the demagnetized plunger in the elution well is performed at a third vertical speed that is faster than both the first and second vertical speeds.

55. The method according to any one of clauses 52-54, wherein the method further comprises one or more mixing steps comprising reciprocating the plunger sufficient to mix the elution buffer prior to removing the plunger in step e).

56. The method according to clause 55, wherein at least one of the one or more mixing steps comprises a pause of the plunger in the elution buffer.

57. The method according to clause 56, wherein during the pause the magnet is inserted into the plunger for a period of time sufficient to allow the magnetic particles to reattach to the remagnetized plunger and then the magnet is removed from the plunger to allow the magnetic particles to disassociate from the plunger into the elution buffer.

58. The method according to any one of clauses 52-57, wherein following elution of the nucleic acid and removal of the plunger the nucleic acid containing elution buffer is removed.

59. The method according to clause 58, wherein removal of the nucleic acid containing elution buffer is performed by pipetting.

60. The method according to any one of clauses 52-59, wherein the volume of elution buffer is between 10 µl and 300 µl.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of eluting nucleic acid from attached magnetic particles, the method comprising:
    a) inserting into an elution well comprising an elution buffer a magnetized plunger comprising magnetically attached magnetic particles comprising attached nucleic acid;
    b) centering the magnetized plunger in the elution well by driving the magnetized plunger against the bottom of the elution well;
    c) retracting a magnet out of the plunger to demagnetize the plunger;
    d) reciprocating the demagnetized plunger up and down in the elution buffer at a first vertical speed sufficient to elute the nucleic acid; and
    e) removing the plunger from the elution buffer at a second vertical speed, wherein the second vertical speed is slower than the first vertical speed.

2. The method according to claim 1, wherein the method further comprises two or more steps of driving the demagnetized plunger to the bottom of the elution well to center the demagnetized plunger in the elution well.

3. The method according to claim 1, wherein the driving the demagnetized plunger to the bottom of the elution well to center the demagnetized plunger in the elution well is performed at a third vertical speed that is faster than both the first and second vertical speeds.

4. The method according to claim 1, wherein the method further comprises one or more mixing steps comprising reciprocating the plunger sufficient to mix the elution buffer prior to removing the plunger in step e).

5. The method according to claim 4, wherein at least one of the one or more mixing steps comprises a pause of the plunger in the elution buffer.

6. The method according to claim 5, wherein during the pause the magnet is inserted into the plunger for a period of time sufficient to allow the magnetic particles to reattach to the remagnetized plunger and then the magnet is removed from the plunger to allow the magnetic particles to disassociate from the plunger into the elution buffer.

7. The method according to claim 1, wherein following elution of the nucleic acid and removal of the plunger the nucleic acid containing elution buffer is removed.

8. The method according to claim 7, wherein removal of the nucleic acid containing elution buffer is performed by pipetting.

9. The method according to claim 1, wherein the volume of elution buffer is between 10 µl and 300 µl.

10. The method according to claim 1, wherein the plunger comprises an elongated hollow cone structure comprising:
    an open top;
    a closed tip comprising an end nub, wherein the end nub protrudes beyond the end of the closed tip so that upon complete insertion of the plunger into the elution well, the end nub contacts the bottom of the elution well and leaves a space between the bottom of the elution well and the closed tip, and wherein the elution well is configured to receive and align the plunger to the center of the elution well when the plunger is inserted into the elution well.

11. The method according to claim 10, wherein the closed tip of the plunger is a closed rounded tip.

12. The method according to claim 10, wherein the plunger comprises a diameter adjacent to the closed tip equal to the smallest diameter of the elution well and a height that is longer than the depth of the elution well.

13. The method according to claim 10, wherein the plunger further comprises a plurality of flutes arranged parallel to the long axis of the elongated hollow cone structure extending from the closed tip.

14. The method according to claim 1, wherein the plunger comprises an elongated hollow cone structure comprising:
   an open top,
   a closed tip,
   a plurality of flutes arranged parallel to the long axis of the elongated hollow cone structure extending from the closed tip, wherein the elution well is configured to receive and align the plunger to the center of the sample processing well when the plunger is inserted into the elution well.

15. The method according to claim 14, wherein the closed tip of the plunger is a closed rounded tip.

16. The method according to claim 14, wherein the plunger comprises a diameter adjacent to the closed tip equal to the smallest diameter of the elution well and a height that is longer than the depth of the elution well.

17. The method according to claim 14, wherein plunger further comprises an end nub that protrudes beyond the end of the closed rounded tip so that upon complete insertion of the plunger into the elution well, the end nub contacts the bottom of the elution well and leaves a space between the bottom of the elution well and the closed rounded tip.

\* \* \* \* \*

UNITED STATES PATENT AND TRADEMARK OFFICE
CERTIFICATE OF CORRECTION

PATENT NO. : 12,018,248 B2
APPLICATION NO. : 17/140854
DATED : June 25, 2024
INVENTOR(S) : Mark Talmer et al.

It is certified that error appears in the above-identified patent and that said Letters Patent is hereby corrected as shown below:

In the Specification

In Column 8, Line 21, delete "HC1," and insert -- HCI, --.

In Column 8, Line 24, delete "HC1," and insert -- HCI, --.

In Column 8, Line 39, delete "a-Hemolysin" and insert -- α-Hemolysin --.

In Column 21, Line 62, after "magnetically" delete -- 5 --.

In Column 30, Line 65, delete "~seconds" and insert -- ~4 seconds --.

In the Claims

In Column 32, Line 54, before "The plunger according" insert -- 18. --.

Signed and Sealed this
Twenty-ninth Day of October, 2024

Katherine Kelly Vidal
*Director of the United States Patent and Trademark Office*